(12) United States Patent
Cambier et al.

(10) Patent No.: US 11,701,361 B2
(45) Date of Patent: Jul. 18, 2023

(54) P110-DELTA INHIBITORS TREAT AND PREVENT AUTOIMMUNITY WHILE SPARING THE ABILITY TO MOUNT AN IMMUNE RESPONSE TO EXOGENOUS IMMUNOGENS

(71) Applicant: THE REGENTS OF THE UNIVERSITY OF COLORADO, Denver, CO (US)

(72) Inventors: John Cambier, Denver, CO (US); Elizabeth Franks, Denver, CO (US)

(73) Assignees: NATIONAL INSTITUTES OF HEALTH (NCH), U.S. DEPT. OF HEALTH AND HUMAN SERVICES (DHHS), U.S. GOVERNMENT NIH DIVISION OF EXTRAMURAL INVENTIONS AND TECHNOLOGY RESOURCES (DEITR), Bethesda, MD (US); THE REGENTS OF THE UNIVERSITY OF COLORADO, Denver, CO (US)

( * ) Notice: Subject to any disclaimer, the term of this patent is extended or adjusted under 35 U.S.C. 154(b) by 63 days.

(21) Appl. No.: 16/959,960

(22) PCT Filed: Jan. 7, 2019

(86) PCT No.: PCT/US2019/012532
§ 371 (c)(1),
(2) Date: Jul. 2, 2020

(87) PCT Pub. No.: WO2019/136373
PCT Pub. Date: Jul. 11, 2019

(65) Prior Publication Data
US 2021/0069197 A1  Mar. 11, 2021

Related U.S. Application Data

(60) Provisional application No. 62/614,040, filed on Jan. 5, 2018.

(51) Int. Cl.
A61K 31/52 (2006.01)
A61P 37/02 (2006.01)
A61P 3/10 (2006.01)

(52) U.S. Cl.
CPC ............... *A61K 31/52* (2013.01); *A61P 3/10* (2018.01); *A61P 37/02* (2018.01)

(58) Field of Classification Search
CPC .................................................. A61K 31/52
See application file for complete search history.

(56) References Cited

U.S. PATENT DOCUMENTS

2010/0029693 A1* 2/2010 Douangpanya ...... A61K 31/517
514/263.21

OTHER PUBLICATIONS

Akerlund, J. et al. "B cell expression of the SH2-containing inositol 5-phosphatase (SHIP-1) is required to establish anergy to high affinity, proteinacious autoantigens." J. Autoimmun. vol. 62; pp. 45-54 (Aug. 2015).
Bi, et al. "Early embryonic lethality in mice deficient in the p110beta catalytic subunit of PI 3-kinase." Mamm. Genome vol. 13; pp. 169-172. (2002).
Bi, et al. "Proliferative defect and embryonic lethality in mice homozygous for a deletion in the p110alpha subunit of phosphoinositide 3-kinase." J. Biol. Chem. vol. 274, No. 16; pp. 10963-10968 (Apr. 1999).
Bilancio, et al. "Key role of the p110delta isoform of PI3K in B-cell antigen and IL-4 receptor signaling: comparative analysis of genetic and pharmacologic interference with p110delta function in B cells." Blood vol. 107, No. 2; pp. 642-650 (Jan. 15, 2006).
Bottini, et al. "A functional variant of lymphoid tyrosine phosphatase is associated with type I diabetes" Nat. Genet, vol. 36, No. 4; pp. 337-338 (Apr. 2004).
Bottini, et al. "Role of PTPN22 in type 1 diabetes and other autoimmune diseases." Semin Immunol vol. 18; pp. 207-213 (2006).
Browne, et al. "Suppression of phosphatidylinositol 3,4,5-trisphosphate production is a key determinant of B cell anergy." Immunity vol. 31; pp. 749-760 (Nov. 20, 2009).
Cambier, "Autoimmunity risk alleles: hotspots in B cell regulatory signaling pathways." J. Clin. Invest. vol. 123, No. 5; pp. 1928-1931 (May 1, 2013).
Chan, et al. "Defective negative regulation of antigen receptor signaling in Lyn-deficient B lymphocytes." Curr. Biol, vol. 8; pp. 545-553 (Apr. 22, 1998).
Chiu, et al. "The Selective Phosphoinoside-3-Kinase p110delta Inhibitor IPI-3063 Potently Suppresses B Cell Survival, Proliferation, and Differentiation" Front. Immunol, vol. 8; art. 747 (Jun. 2017).
Chung, et al. "PTPN22: its role in SLE and autoimmunity." Autoimmunity vol. 40; pp. 582-590 (Dec. 2007).
Clayton, et al. "A crucial role for the p110delta subunit of phosphatidylinositol 3-kinase in B cell development and activation." J. Exp. Med. vol. 196, No. 6; pp. 753-763 (Sep. 16, 2002).
Coutre, et al. "Management of adverse events associated with idelalisib treatment: expert panel opinion." Leuk. Lymphoma vol. 56; pp. 2779-2786 (Oct. 2015).
Cyster, et al. "Competition for follicular niches excludes self-reactive cells from the recirculating B-cell repertoire." Nature vol. 371: pp. 389-395 (Sep. 29, 1994).

(Continued)

*Primary Examiner* — Paul V Ward
(74) *Attorney, Agent, or Firm* — Adsero IP

(57) ABSTRACT

Methods of using a phosphoinositide 3-kinase p110-delta inhibitor to treat, delay the onset, or slow the progression of an autoimmune disease or disorder in a subject, without suppressing the subject's B cell responses to exogenous antigens or rendering the subject immunocompromised, as well as pharmaceutical compositions containing phosphoinositide 3-kinase p110-delta inhibitors in amounts suitable for convenient and accurate administration within these therapeutic methods.

10 Claims, 15 Drawing Sheets

(56) References Cited

OTHER PUBLICATIONS

Franks, et al. "A Precision B cell-targeted Therapeutic Approach to Autoimmunity Caused by PI3K Pathway Dysregulation." J. Immunol. vol. 202; pp. 3381-3393 (May 2019).
Gauld, et al. "Maintenance of B cell anergy requires constant antigen receptor occupancy and signaling." Nat. Immunol. vol. 6; pp. 1160-1167 (Nov. 2005).
Gay, et al. "Receptor editing: an approach by autoreactive B cells to escape tolerance." J. Exp. Med. vol. 177; pp. 999-1008 (Apr. 1993).
Getahun, A. et al. "Continuous inhibitory signaling by both SHP-1 and SHIP-1 pathways is required to maintain unresponsiveness of anergic B cells." J Exp Med vol. 213; pp. 751-769 (2016).
Goodnow, et al. "Breakdown of self-tolerance in anergic B lymphocytes." Nature vol. 352; pp. 532-536 (Aug. 8, 1991).
Goodnow, et al. "Induction of self-tolerance in mature peripheral B lymphocytes." Nature vol. 342; pp. 385-391 (Nov. 23, 1989).
Halverson, et al. "Receptor editing is the main mechanism of B cell tolerance toward membrane antigens" Nat. Immunol. vol. 5; pp. 645-650 (Jun. 2004).
Herman, et al. "Phosphatidylinositol 3-kinase-delta inhibitor CAL-101 shows promising preclinical activity in chronic lymphocytic leukemia by antagonizing intrinsic and extrinsic cellular survival signals." Blood v. 116; pp. 2078-2088 (2010).
Horak, et al. "Randomized phase 1 study of the phosphatidylinositol 3-kinase delta inhibitor idelalisib in patients with allergic rhinitis" J. Allergy Clin. Immunol. vol. 137; iss. 6; pp. 1733-1741 (Jun. 1, 2016).
Huck, et al. "Expression of B cell receptor-associated signaling molecules in human lupus." Autoimmunity vol. 33; pp. 213-224 (2001).
Jackson, et al. "B cells take the front seat: dysregulated B cell signals orchestrate loss of tolerance and autoantibody production." Curr. Opin. Immunol. vol. 33; pp. 70-77 (Apr. 2015).
Jou, et al. "Essential, nonredundant role for the phosphoinositide 3-kinase p110delta in signaling by the B-cell receptor complex." Mol. Cell. Biol. vol. 22, iss. 24; pp. 8580-8591 (Dec. 15, 2002).
Lannutti, et al. "CAL-101, a p110delta selective phosphatidylinositol-3-kinase inhibitor for the treatment of B-cell malignancies, inhibits PI3K signaling and cellular viability." Blood vol. 117; No. 2; pp. 591-594 (Jan. 13, 2011).
Lu, et al. "Genetic associations of LYN with systemic lupus erythematosus." Genes Immun. vol. 10; pp. 397-403 (2009).
Manjarrez-Orduno, et al. "CSK regulatory polymorphism is associated with systemic lupus erythematosus and influences B-cell signaling and activation." Nat. Genet. vol. 44; pp. 1227-1230 (Nov. 2012).
Miller, et al. "FDA approval: idelalisib monotherapy for the treatment of patients with follicular lymphoma and small lymphocytic lymphoma." Clin. Cancer Res. vol. 21; pp. 1525-1529 (Apr. 1, 2015).
Morris, et al. "Genome-wide association meta-analysis in Chinese and European individuals identifies ten new loci associated with systemic lupus erythematosus." Nat. Genet. vol. 48; pp. 940-946 (Aug. 2016).
Mustelin, et al. "Protein tyrosine phosphatases and the immune response" Nat Rev Immunol vol. 5; pp. 43-57 (Jan. 2005).
Nemazee, et al. "Clonal deletion of B lymphocytes in a transgenic mouse bearing anti-MHC class I antibody genes." Nature vol. 337; pp. 562-566 (Feb. 9, 1989).
Nossal, et al. "Clonal anergy: persistence in tolerant mice of antigen-binding B lymphocytes incapable of responding to antigen or mitogen." Proc. Natl. Acad. Sci. USA vol. 77; pp. 1602-1606 (Mar. 1980).
Okkenhaug, "Signaling by the phosphoinositide 3-kinase family in immune cells" Annu. Rev. Immunol. vol. 31; pp. 675-704 (2013).
Okkenhaug, et al. "Impaired B and T cell antigen receptor signaling in p110delta PI 3-kinase mutant mice." Science vol. 297; pp. 1031-1034 (Aug. 9, 2002).
Okkenhaug, et al. "PI3K in lymphocyte development, differentiation and activation." Nat Rev Immunol vol. 3; pp. 317-330 (Apr. 2003).
O'Neill, et al. "Monophosphorylation of CD79a and CD79b ITAM motifs initiates a SHIP-1 phosphatase-mediated inhibitory signaling cascade required for B cell anergy." Immunity vol. 35; pp. 746-756 (Nov. 23, 2011).
Packard, et al. "B lymphocyte antigen receptor signaling: initiation, amplification, and regulation." F1000Prime Rep, vol. 5:40; 8 pages (Oct. 1, 2013).
Pagel, et al. "The changing landscape in the frontline treatment of chronic lymphocytic leukemia." Clin. Adv. Hematol. Oncol. vol. 14; iss. 5, supp. 8; pp. 1-15. (May 2016).
Sasaki, et al. "Function of PI3Kgamma in thymocyte development, T cell activation, and neutrophil migration" Science vol. 287; pp. 1040-1046 (Feb. 11, 2000).
Schaeffer, et al. "Requirement for Tec kinases Rlk and Itk in T cell receptor signaling and immunity." Science vol. 284; pp. 638-641 (Apr. 23, 1999).
Smith, et al. "Elevated PTEN expression maintains anergy in human B cells and reveals unexpectedly high repertoire autoreactivity." JCI Insight vol. 4, iss. 3; e123384 (Feb. 7, 2019).
Stagakis, et al. "Identification of novel microRNA signatures linked to human lupus disease activity and pathogenesis: miR-21 regulates aberrant T cell responses through regulation of PDCD4 expression." Ann. Rheum. Dis. vol. 70, pp. 1496-1506 (2011).
Tiegs, et al. "Receptor editing in self-reactive bone marrow B cells." J. Exp. Med. vol. 177; pp. 1009-1020 (Apr. 1993).
Wu, et al. "Defective PTEN regulation contributes to B cell hyperresponsiveness in systemic lupus erythematosus." Sci. Transl. Med. vol. 6, iss. 246, ra299; pp. 1-13 (Jul. 23, 2014).

\* cited by examiner

P110-DELTA INHIBITORS TREAT AND PREVENT AUTOIMMUNITY WHILE SPARING THE ABILITY TO MOUNT AN IMMUNE RESPONSE TO EXOGENOUS IMMUNOGENS

CROSS-REFERENCE TO RELATED APPLICATION

This application claims priority to and is a 35 U.S.C. § 371 national phase application of PCT/US2019/012532 (WO2019/136373), filed on Jan. 7, 2019 entitled "P-110-DELTA INHIBITORS TREAT AND PREVENT AUTOIMMUNITY WHILE SPARING THE ABILITY TO MOUNT AN IMMUNE RESPONSE TO EXOGENOUS IMMUNOGENS", which application claims priority to and the benefit of U.S. Provisional Application No. 62/614,040, filed Jan. 5, 2018, the disclosures of which are incorporated herein by reference in their entirety.

STATEMENT OF FEDERALLY SPONSORED RESEARCH

This invention was made with government support under grant numbers R01AI124487 and R01DK096492 awarded by the National Institutes of Health. The U.S. government has certain rights in the invention.

TECHNICAL FIELD

This invention relates generally to methods of using a phosphoinositide 3-kinase p110-delta (PI3K-p110δ) inhibitor to treat, delay the onset, or slow the progression of an autoimmune disease or disorder in a subject.

BACKGROUND

Phosphoinositide 3-kinases (PI3K) are lipid kinases that phosphorylate lipids at the 3-hydroxyl residue of the inositol ring of phosphoinositides. PI3 kinase is a heterodimer consisting of p85 and p110 subunits. Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct. p110δ and p110γ are restricted in expression to the lymphoid compartment with nonredundant, nonoverlapping roles, whereas p110α and p110β are ubiquitously expressed and removal of these subunits results in embryonic lethality. There is a growing body of evidence indicating that p110δ is the functionally dominant isoform utilized in B cell antigen receptor (BCR) signaling.

PI3Kδ protein (also referred to as p110δ or p110-delta) is a 1044 amino acid member of PI3K class IA, encoded by the human PIK3CD gene which was mapped to chromosome 1p3.2. The p110δ isoform has been implicated in biological functions related to immune-inflammatory diseases, including signaling from the B cell receptor, T cell receptor, FcR signaling of mast cells and monocyte/macrophage, and osteoclast function/RANKL signaling. Deletion of the PI3Kδ gene or selective introduction of a catalytically inactive mutant of PI3Kδ causes a nearly complete ablation of B cell proliferation and signaling, and impairment of signaling through T cell receptors as well.

Multiple mechanisms are involved in the maintenance of B cell tolerance to autoantigens. In the bone marrow, receptor editing and clonal deletion ensure that B cells undergoing high avidity interactions with self-antigens are removed from the repertoire. However, B cells recognizing lower avidity self-antigens do not undergo receptor editing, but instead are released into the periphery where they are maintained transiently in an unresponsive state called anergy. Anergy is rapidly reversible, requiring chronic receptor stimulation by self-antigen, suggesting maintenance by nondurable biochemical mechanisms.

Maintenance of the anergic state of peripheral autoreactive B cells involves multiple regulatory mechanisms that operate proximally in BCR signaling. Among these are inositol lipid phosphatases, PTEN and SHIP-1 that, in anergic cells prevent the BCR-mediated accumulation of PI(3,4,5)P3. Acute deletion of SHIP-1 or PTEN and expression of a constitutively-active catalytic subunit of PI3K in anergic B cells leads to immediate loss of anergy followed by cell proliferation, differentiation, and production of autoantibodies, thus demonstrating the importance of these proteins and their regulation of the PI3K pathway in maintaining B cell anergy. Importantly, B cells from SLE, Type 1 Diabetes (T1D), and Autoimmune Thyroiditis (AITD) patients express reduced levels of PTEN, consistent with a role in autoimmunity.

There remains an unmet need for effective treatments of autoimmune diseases and disorders.

SUMMARY

The inventors have unexpectedly discovered that administration of low doses of PI3K-p110δ inhibitors compensate for failed PI3K pathway regulation, and thereby delay development of autoimmunity in a murine model of type 1 diabetes. Surprisingly, the chronically treated animals remained immunocompetent as indicated by production of class switched high affinity antibodies in response to immunization. Low dose p110δ inhibition selectively inhibited participation in autoimmunity of autoreactive B cells that have lost anergy due to defective PI3K pathway regulation and did not affect in vitro or in vivo T cell responses.

Thus, this disclosure provides methods of treating autoimmune disorders by modifying B cell antigen receptor signaling to prevent or significantly reduce responses to self or endogenous antigens while ensuring that protective immunological responses are mounted against exogenous pathogens. These methods comprise administering compounds with inhibitory activity and selective binding to the p110 delta isoform of the PI3 kinase ("PI3K-p110δ inhibitors"). An exemplary PI3K-p110δ inhibitor for use in these methods is idelalisib. In these methods, the PI3K-p110δ inhibitor may be administered in a dosage or administration schedule that treats, prevents, and/or delays the onset of an autoimmune disorder while sparing B cell responses to exogenous antigens.

In these methods, the PI3K-p110δ inhibitors may be used for in vitro, in situ, and in vivo diagnosis or treatment of mammalian cells, organisms, or associated pathological autoimmune conditions, such as autoimmune diabetes mellitus (type 1 diabetes mellitus; T1D), systemic lupus erythematosus, autoimmune thyroiditis, rheumatoid arthritis, psoriasis, and multiple sclerosis.

These methods may therefore include treating or delaying the onset or slowing the progression of an autoimmune disease or disorder in a subject by administering a therapeutically effective amount of a phosphoinositide 3-kinase p110-delta (PI3K-p110δ) inhibitor to the subject at a dosage that does not reduce immune response to exogenous immunogens in the subject. In these methods, the PI3K-p110δ inhibitor may be idelalisib. The idelalisib may be administered at a dosage of between about 0.23 mg/kg/day and about 3.6 mg/kg/day, or between about 0.45 mg/kg/day and about 1.8 mg/kg/day, or between about 0.9 mg/kg/day and about 1.8 mg/kg/day, or between about 1.8 mg/kg/day and about 3.6 mg/kg/day. The idelalisib may be administered at a dosage of about 0.9 mg/kg/day, or about 1.8 mg/kg/day.

In these methods, the autoimmune disease or disorder may be selected from autoimmune diabetes mellitus (type 1 diabetes mellitus; TID), systemic lupus erythematosus, autoimmune thyroiditis, rheumatoid arthritis, psoriasis, and multiple sclerosis. In exemplary methods, the autoimmune disease is type 1 diabetes mellitus (TID).

In these methods, the PI3K-p110δ inhibitor may be administered to a subject displaying reduced activity of phosphatase and tensin homolog (PTEN) in B cells.

In these methods, the PI3K-p110δ inhibitor may be administered to a subject displaying reduced activity of the SH-2-containing inositol phosphatase SHIP-1 in B cells.

Another aspect of the invention provides the use of a PI3K-p110δ inhibitor in the manufacture of a medicament for treating an autoimmune disease or disorder, in particular an autoimmune disorder that may be mediated by PI3 kinase including by selective inhibition of the p110 delta isoform.

These methods and uses may further comprise administering an additional therapeutic agent, such as an antiinflammatory agent, an immunomodulatory agent, an antidiabetic agent, and/or an agent for treating immunodeficiency disorders.

Another aspect of the invention provides a pharmaceutical composition comprising a PI3K-p110δ inhibitor and a pharmaceutically acceptable carrier, glidant, diluent, and/or excipient. In these pharmaceutical compositions, the PI3K-p110δ inhibitor is preferably present in a dose that can be easily and accurately administered to a subject to treat, prevent, and/or delay the onset of an autoimmune disorder while sparing B cell responses to exogenous antigens. An exemplary PI3K-p110δ inhibitor that may be present in these pharmaceutical compositions is idelalisib. An exemplary oral dosage formulation of idelalisib for use in the therapeutic methods of this disclosure includes idelalisib in an amount between 5 mg and 25 mg Another aspect of the invention provides a kit for treating an autoimmune disease or disorder mediated by the p110 delta isoform of PI3 kinase, comprising a pharmaceutical composition comprising a PI3K-p110δ inhibitor, such as idelalisib, and instructions for use.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

BRIEF DESCRIPTION OF FIGURES

FIG. 1A is a schematic representation of the survival experimental protocol. FIG. 1B shows disease incidence as measured by % non-diabetic (blood glucose <600 mg/d1) mice receiving vehicle control chow (black line) or 0.9375 mg/kg Idelalisib containing chow (grey line) (n=25/group). FIG. 1C is a schematic representation of the immunization experimental protocol. FIG. 1D shows the total NP-specific (NP27 binding) and high affinity NP-specific (NP2 binding) IgM (left) and IgG (right) antibody secreting cell response (ASCs/Spleen) 14 days post immunization of mice receiving vehicle control chow (white bar) or 0.9375 mg/kg Idelalisib chow (grey bar) (n=7/group. Error bars represent mean±SEM). FIG. 1E shows the total circulating NP-specific (NP27 binding) IgM (left) and IgG (center) and high affinity NP-specific (NP2 binding) IgG (right) at day 14 post-immunization of mice receiving vehicle control chow (white bars) or 0.9375 mg/kg Idelalisib containing chow (grey bars). (Idel=idelalisib. BG=blood glucose. Bars in FIGS. 1D & 1E represent mean±SEM. Log-rank (Mantel-Cox) test was used to calculate statistics in FIG. 1B. One-Way ANOVA was used to calculate statistics in FIGS. 1D & 1E. *=p<0.05, =p<0.01, *=p<0.005, ****=p<0.0001).

FIG. 2A is a schematic representation of the experimental protocol. FIG. 2B shows WT Ars/A1 or PTEN$^{fl/wt}$×SHIP-1$^{fl/wt}$ Ars/A1-derived IgM$^a$ anti-Ars antibody detected in serum 14 days post tamoxifen treatment of mice receiving vehicle control chow (open circles), 0.9375 mg/kg (closed squares), 3.75 mg/kg (closed triangles), 30 mg/kg (closed circles) and WT Ars/A1 receiving 0 mg/kg (open triangles) idelalisib-containing chow. FIG. 2C shows quantification of relative response of PTEN$^{fl/wt}$×SHIP-1$^{fl/wt}$ Ars/A1-derived IgM$^a$ anti-Ars antibody detected in the serum 14 days post tamoxifen treatment. FIG. 2D shows quantification of relative response of PTEN$^{fl/wt}$×SHIP-1$^{fl/wt}$ Ars/A1-derived IgM$^a$ anti-Ars ASCs/spleen 14 days post tamoxifen treatment. FIG. 2E shows proliferation (top row) and plasmablast differentiation (bottom row) of splenic Ars/A1 Idiotype+ YFP+ B cells of mice on vehicle control chow (open black line, top row) or indicated doses of idelalisib (shaded line, top row) 14 days post tamoxifen treatment. Enumeration of (FIG. 2F) total recovered transferred PTEN$^{fl/wt}$×SHIP-1$^{fl/wt}$ cells, (FIG. 2G) the unproliferated Ars/A1 Idiotype+ YFP+ population and (FIG. 2H) plasmablasts in the spleens of recipient mice 14 days post tamoxifen treatment (For FIGS. 2E, 2F, 2G, & 2H gated on: B220+ Ars/A1 Id+ YFP+). (Idel:=idelalisib. n=8/group. Data shown are representative of at least three replicated experiments. Bars in FIGS. 2C, 2D, 2F, 2G, & 2H represent mean±SEM. One-Way ANOVA was used to calculate statistics in FIGS. 2C, 2D, 2F, 2G, & 2H. *=p<0.05, =p<0.01, *=p<0.005, ****=p<0.0001, ND=undetectable).

FIG. 3A schematic representation of the experimental protocol. FIG. 3B shows WT Ars/A1 or SHP-1$^{fl/fl}$ Ars/A1-derived IgM$^a$ anti-Ars antibody detected in serum 14 days post tamoxifen treatment of mice receiving vehicle control chow (open circles), 0.9375 mg/kg (closed squares), 3.75 mg/kg (closed triangles), 30 mg/kg (closed circles) or WT Ars/A1 receiving 0 mg/kg (open triangles) idelalisib-containing chow. FIG. 3C shows quantification of relative response of SHP-1$^{fl/fl}$ Ars/A1-derived IgM$^a$ anti-Ars antibody detected in the serum 14 days post tamoxifen treatment. FIG. 3D shows quantification of relative response of SHP-1$^{fl/fl}$ Ars/A1-derived IgM$^a$ anti-Ars ASCs/spleen 14 days post tamoxifen treatment. FIG. 3E shows proliferation (top row) and plasmablast differentiation (bottom row) of splenic Ars/A1 Idiotype+ CD45.1+ B cells of mice on vehicle control chow (open black line, top row) or indicated doses of idelalisib (shaded line, top row). Enumeration of (FIG. 3F) total recovered transferred SHP-1$^{fl/fl}$ cells, (FIG. 3G) the unproliferated Ars/A1 Idiotype+ CD45.1+ population and (FIG. 3H) plasmablasts in the spleens of recipient mice 14 days post tamoxifen treatment (For FIGS. 3E, 3F, 3G, & 3H gated on: B220+ Ars/A1 Id+ CD45.1+). (Idel:=idelalisib. n=8/group. Data shown are representative of at least three replicated experiments. Bars in FIGS. 3C, 3D, 3F, 3G, & 3H represent mean±SEM. One-Way ANOVA was used to calculate statistics in FIGS. 3C, 3D, 3F, 3G, & 3H. *=p<0.05, =p<0.01, *=p<0.005, ****=p<0.0001, ND=undetectable).

FIG. 4A shows calcium flux of B220+ cells stimulated with anti-H&L with simultaneous addition of 0 nM (black line), 15 nM (solid grey line), 60 nM (grey long dashed line) or 490 nM (grey dashed line) idelalisib. FIG. 4B shows quantification of area under the curve (AUC) seen in FIG. 4A. FIG. 4C shows quantification of phosphorylated signaling intermediaries after preincubation with indicated doses of idelalisib and BCR stimulation. (idel:=idelalisib. n=5/group. Data shown are representative of at least three replicated experiments. Bars in FIGS. 4B & 4C represent mean±SEM. Student T test was used to calculate statistics in FIG. 4B. One-Way ANOVA was used to calculate statistics in FIG. 4C. *=p<0.05, =p<0.01, *=p<0.005, ****=p<0.0001).

FIG. 5A is a schematic representation of the experimental protocol. FIG. 5B shows enumeration of total recovered transferred MD4 B cells and (FIG. 5C) quantification of the unproliferated population of recovered MD4+ B cells in the spleen of recipient mice 5 days post-immunization. FIG. 5D shows MD4-derived IgM$^a$ anti-HEL antibody detected in serum 5 days post immunization of mice receiving vehicle control chow (open circles), 0.9375 mg/kg (closed squares), 3.75 mg/kg (closed triangles), 30 mg/kg (closed circles), and unimmunized mice receiving 0 mg/kg (open triangles) idelalisib-containing chow. FIG. 5E shows quantification of relative response of MD4-derived IgM$^a$ anti-HEL antibody detected in serum and (FIG. 5F) MD4-derived IgM$^a$ anti-HEL ASCs/spleen 5 days post immunization. FIG. 5G shows proliferation of splenic MD4+ B cells 5 days post-immunization of mice receiving vehicle control chow (unfilled black line) or indicated doses of idelalisib (shaded grey line). (Idel:=idelalisib.–imm=unimmunized. n=8/group. Data shown are representative of at least three replicated experiments. FIGS. 5B, 5C, & 5G gated on: B220+ HEL binding+. Bars in FIGS. 5B, 5C, 5E, & 5F represent mean±SEM. One-Way ANOVA was used to calculate statistics. *=p<0.05, =p<0.01, *=p<0.005, ****=p<0.0001).

FIG. 6A shows calcium flux of CD4+ T cells stained with anti-CD3 biotin with simultaneous addition of 0 nM (black line) or 15 nM (grey line) Idelalisib, and crosslinked with avidin. FIG. 6B shows quantification of area under the curve of A. FIG. 6C is a schematic representation of the experimental protocol. FIG. 6D shows representative flow cytometric plots of proliferation (CFSE) and upregulation of CD44 following immunization. FIG. 6E shows representative histogram (left) and quantification (right) of proliferation (CFSE) of recovered OT-II T cells from the spleens of recipient mice. FIG. 6F shows representative histogram (left) and quantification (right) of upregulation of CD44 of recovered OT-II T cells from the spleens of recipient mice. (Idel:=idelalisib. imm+/−=immunized/unimmunized. n=5/group. Bars in FIGS. 6B, 6E, & 6F represent mean±SEM. Students T test was used to calculate statistics in B. One-Way ANOVA was used to calculate statistics in FIGS. 6E & 6F. *=p<0.05, =p<0.01, *=p<0.005, ****=p<0.0001).

DETAILED DESCRIPTION

Figure 1A:
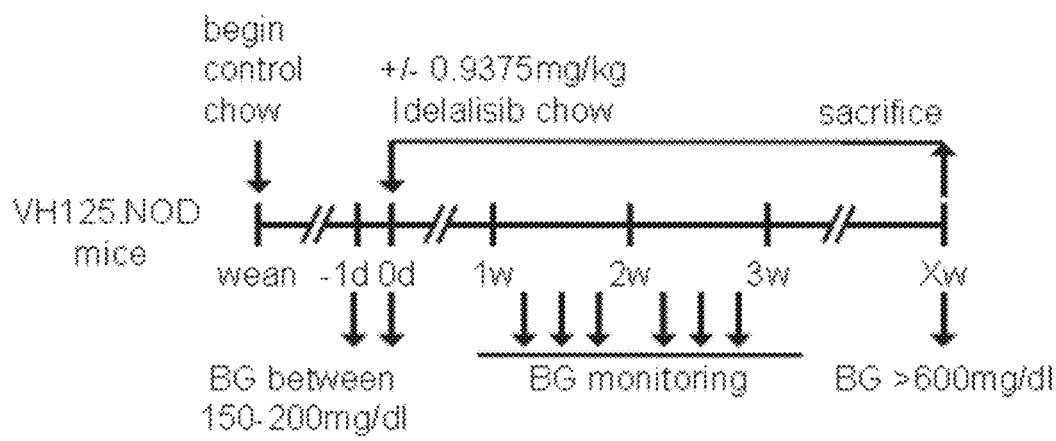
FIGS. 1A-1E show low dose idelalisib delays disease progression in VH125.NOD mice without compromising response to immunization.

In the description that follows, a number of terms are used and the following definitions are provided to facilitate understanding of the claimed subject matter. Terms that are not expressly defined herein are used in accordance with their plain and ordinary meanings. Abbreviations used herein have their conventional meaning within the chemical and biological arts.

Unless otherwise specified, "a" or "an" means "one or more."

The term "about" is used herein to mean plus or minus ten percent (10%) of a value. For example, "about 100" refers to any number between 90 and 110.

When ranges are used herein for physical properties, such as molecular weight, or chemical properties, or dosage amounts, all combinations and subcombinations of ranges and specific embodiments therein are intended to be included.

The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The terms "coadministration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a PI3K-p110δ inhibitor that is sufficient to affect the intended application, including but not limited to disease treatment, prevention, or delay, as defined below. The therapeutically effective amount may vary depending upon the intended application (in vitro or in vivo), or the subject and disease condition being treated, e.g., the weight and age of the subject, the severity of the disease condition, the manner of administration and the like, which can be determined by one of ordinary skill in the art. The term also applies to a dose that will induce a particular response in target cells, e.g. reduction of B cell proliferation or activation, and/or stabilization of B cell anergy. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refer to an approach for obtaining beneficial or desired results including but not limited to, therapeutic benefit and/or a prophylactic benefit. By therapeutic benefit is meant eradication or amelioration of the underlying autoimmune disorder being treated. Also, a therapeutic benefit is achieved with the eradication or amelioration of one or more of the physiological symptoms associated with the underlying autoimmune disorder such that an improvement is observed in the patient, notwithstanding that the patient may still be afflicted with the underlying autoimmune disorder. For prophylactic benefit, the pharmaceutical compositions may be administered to a patient at risk of developing a particular disease, or to a patient reporting one or more of the physiological symptoms of an autoimmune disease, even though a diagnosis of this disease may not have been made.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T cells. Chronic inflammatory diseases, the rejection of solid transplanted tissue and organs, e.g., kidney and bone marrow transplants, and graft versus host disease (GVHD), are further examples of inflammatory reactions of the specific defense system.

"Inflammatory cell activation" refers to the induction by a stimulus (including, but not limited to, cytokines, antigens or autoantibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

A "therapeutic effect" encompasses a therapeutic benefit and/or a prophylactic benefit as described above. A prophylactic effect includes delaying or eliminating the appearance (i.e., slowing the onset) of an autoimmune disease or condition, delaying or eliminating the onset of symptoms of an autoimmune disease or condition, slowing, halting, or reversing the progression of an autoimmune disease or condition, or any combination thereof.

The term "subject" or "patient" refers to a mammal, for example a human, mouse, rat, dog, cat, horse, or pig. The methods described herein can be useful in both human therapeutics and veterinary applications. It is not intended that the term be limited to a particular age or sex. Thus, adult and newborn subjects, as well as fetuses, whether male or female, are encompassed by the term. Doses given herein are for humans, but can be adjusted to the size of other mammals, as well as children, in accordance with weight or square meter size.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Autoimmune disease" as used herein refers to any group of disorders in which tissue injury is associated with humoral or cell-mediated responses to the body's own constituents. Exemplary autoimmune disorders that are amenable to treatment in the methods of this disclosure include autoimmune diabetes mellitus (type 1 diabetes mellitus; TID), systemic lupus erythematosus, autoimmune thyroiditis, rheumatoid arthritis, psoriasis, and multiple sclerosis.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "in vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PI3-kinase p110δ selective inhibitor for a given indication, cell type, individual, and other parameters. Information gleaned from such use may be used for experimental or diagnostic purposes or in the clinic to set protocols for in vivo treatment or to select patients for treatment using the methods of this disclosure.

PI3K-p110δ Inhibitor Compounds

The PI3K-p110δ inhibitor compounds useful in the methods of this disclosure may exhibit one or more functional characteristics disclosed herein. For example, the PI3K-p110δ inhibitor compounds may bind specifically to a PI3 kinase with an IC50 for the 110δ isoform of less than about 1 μM, less than about 100 nM, less than about 50 nM, less than about 10 nM, less than about 1 nM, less than about 0.5 nM, less than about 100 pM, or less than about 50 pM. As an additional example, these PI3K-p110δ inhibitor compounds may selectively inhibit one or more members of type I or class I phosphatidylinositol 3-kinases with an IC50 value of about 100 nM or less, about 50 nM or less, about 10 nM or less, about 5 nM or less, about 100 pM or less, about 10 pM or less, or about 1 pM or less as measured in an in vitro kinase assay. As an additional example, the PI3K-p110δ inhibitor compounds may selectively inhibit one or more members of type I PI3-kinases or more type I PI3-kinase mediated signaling pathways, with an IC50 with respect to a p110δ isoform, that is at least 10-fold lower, at least 20-fold lower, at least 50-fold lower, at least 100-fold lower, at least 1000-fold lower than the inhibitor's IC50 with respect to the other isoforms of type I PI3-kinases.

The PI3K-p110δ inhibitor compounds useful in the methods of this disclosure may include any PI3K-p110 delta-specific inhibitor compound, including those disclosed in U.S. Patent Pub. Nos. 2011/0021497; 2012/0245144; 2013/0344061; 2014/0011819; 2015/0011569; 2015/0272936; 2016/0207929; 2016/0222012; or U.S. Pat. Nos. 6,518,277; 60,744,269; 60,744,270, each of which are incorporated herein by reference.

Idelalisib is a reversible p110δ inhibitor that noncovalently binds the ATP binding pocket of the catalytic subunit and targets the p110δ isoform with 110-453 fold more selectivity than other class 1 isoforms. Thus, idelalisib is an exemplary PI3K-p110δ inhibitor compound useful in the methods of this disclosure. Idelalisib (5-fluoro-3-phenyl-2-[(1S)-1-(7H-purin-6-ylamino)propyl]-4(3H)-quinazolinone; or CAL-101), a PI3Kδ inhibitor marketed under the tradename ZYDELIG™ by Gilead Sciences, Inc. ZYDELIG™, is indicated for the treatment of patients with chronic lymphocytic leukemia, in combination with rituximab, in patients for whom rituximab alone would be considered appropriate therapy due to other co-morbidities. It is also indicated for treating patients with relapsed follicular B-cell non-Hodgkin lymphoma in patients who have received at least two prior systemic therapies and patients with relapsed small lymphocytic lymphoma in patients who have received at least two prior systemic therapies. The doses of idelalisib (30 mg/kg) used in these approved applications significantly depletes B cells, and a black box warning has been issued for fatal and/or severe colitis, pneumonitis, and infection following the administration of idelalisib at these doses. Idelalisib is disclosed in U.S. Pat. No. RE44638, International Publication Nos. WO2013/134288, WO2015/014315, WO2015/092810, and WO2005/113556, and US Patent Pub. Nos. 2018/0093987, 2018/0064714, 2018/0037584, and 2017/0260186, each of which is incorporated herein by reference.

Therapeutic Treatment

This disclosure provides methods of treating a subject by administering a therapeutically effective amount of a PI3K-p110δ inhibitor, as described herein, to a subject. Diseases that may be treated with the PI3K-p110δ inhibitor include, but are not limited to, autoimmune disease or disorder such as autoimmune diabetes mellitus (type 1 diabetes mellitus; TID), systemic lupus erythematosus, autoimmune thyroiditis, rheumatoid arthritis, psoriasis, and multiple sclerosis. In exemplary embodiments, the autoimmune disease is type 1 diabetes mellitus (TID). In other embodiments PI3K-p110δ inhibitors can be used to treat immune system dysfunction (e.g., graft-versus-host disease, organ transplant rejection).

Autoimmune diseases that may be treated with PI3K-p110δ inhibitors, such as idelalisib, in the methods of this disclosure may include acute type 1 diabetes mellitus, systemic lupus erythematosus, multiple sclerosis, idiopathic thrombocytopenic purpura, chronic idiopathic thrombocytopenic purpura, dermatomyositis, Sydenham's chorea, myasthenia gravis, lupus nephritis, rheumatic fever, polyglandular syndromes, bullous pemphigoid, Henoch-Schonlein purpura, post-streptococcal nephritis, erythema nodosum, Takayasu's arteritis, ANCA-associated vasculitides, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

Optimal dosing of PI3K-p110δ inhibitors, such as idelalisib, in the methods of this disclosure may include a dosage of between 0.01 mg/kg and 4 mg/kg, preferably given either daily, twice daily, or every other day. The dosage may be up to 10 mg/kg. Exemplary dosages may include between 0.23 mg/kg/day and about 3.6 mg/kg/day, including dosages of idalisib administered at a dosage of between about 0.45 mg/kg/day and about 1.8 mg/kg/day, between about 0.9 mg/kg/day and about 1.8 mg/kg/day, between about 1.8 mg/kg/day and about 3.6 mg/kg/day, or a dosage of idelalisib of about 0.9 mg/kg/day or about 1.8 mg/kg/day. Thus, the individual dose of PI3K-p110δ inhibitors, such as idelalisib, in the methods of this disclosure may include a dosage of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg. The person of ordinary skill will realize that a variety of factors, such as age, general health, specific organ function or weight, as well as effects of prior therapy on specific organ systems (e.g., bone marrow) may be considered in selecting an optimal dosage of the PI3K-p110δ inhibitor, and that the dosage and/or frequency of administration may be increased or decreased during the course of therapy. The dosage may be repeated as needed, with evidence of anergy or autoimmune treatment or abatement observed after as few as 2 to 10 doses. The optimized dosages and schedules of administration disclosed herein show unexpected efficacy and reduced toxicity in treated subjects, while sparing B cell responses to exogenous antigen in the subject.

The dosage of the PI3K-p110δ inhibitor is preferably administered multiple times, once or twice a day, or a week. The schedule of administration may comprise administration once or twice a day, on a cycle selected from the group consisting of: (i) daily; (ii) every other day; (iii) one day of therapy followed by two, three, or four days off; (iv) two days of therapy followed by one, two, three or four days off; (v) three days of therapy followed by one, two, three, four or five days off; (vi) four days of therapy followed by one, two, three, four, or five days off; (vii) five days of therapy followed by one, two, three, four, or five days off; and (viii) weekly or monthly. Such administration cycles may be repeated 4, 6, 8, 10, 12, 16, or 20 times, or more.

Suitable routes of administration of the PI3K-p110δ inhibitor, such as idelalisib, within the methods of this disclosure include, without limitation, oral, parenteral, subcutaneous, rectal, transmucosal, intestinal administration, intramuscular, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into an organ or joint.

Diagnostic assays may be employed in the therapeutic methods of this disclosure to identify subjects with activated PI3K or reduced SH2-containing inositol lipid phosphatase (SHIP-1) and/or reduced phosphatase and tensin homolog (PTEN) expression or activity, particularly in B cells from the subject, defining a subject most likely to respond to PI3K-p110δ inhibitor therapy. Therefore, the inhibition of PI3K-p110δ in cells with low or absent PTEN and/or SHIP-1 expression and activity may be an effective autoimmune disease treatment strategy. Such selection of patients based on PTEN and SHIP-1 activity may also be useful in the clinical evaluation of efficacy of existing or future PI3K inhibitors, as well as in the future prescription of such drugs to patients diagnosed or suspected of having an autoimmune disease or disorder. Accordingly, this disclosure also provides methods for selecting a patient suitable for PI3K-p110δ inhibitor therapy by obtaining at least one biological sample from a subject that is a candidate for therapy with a PI3K-p110δ inhibitor, such as idelalisib, and detecting the activity of PTEN and/or SHIP-1 in the sample, in particular the expression of these proteins in B cells in the sample, thereby identifying the subject with reduced or absent phosphatase activity as particularly suitable for PI3K-p110δ inhibitor therapy.

Methods of determining the presence or absence of PTEN and/or SHIP-1 expression, mutations, and activity in a patient and/or a tumor cell are known in art, for example as described in U.S. Patent Pub. No. 2018/0338977, which is incorporated herein by reference for this purpose.

Thus, one aspect of this disclosure is a method of treating an autoimmune disease or disorder in a subject expressing low or absent PTEN and/or SHIP-1 protein (e.g., B cells displaying low or absent enzymatic activity or gene expression) by administering a PI3K-p110δ inhibitor, or pharmaceutical composition comprising a PI3K-p110δ inhibitor, to the subject. Said another way, these methods include testing a subject and/or a biological sample from a subject for PTEN and SHIP-1 activity, expression and/or mutations, and treating an autoimmune disease or disorder in the subject in which PTEN and/or SHIP-1 protein activity and/or expression is low (i.e., below wild-type expression or protein activity levels) or absent by administering a PI3K-p110δ inhibitor, or pharmaceutical composition comprising a PI3K-p110δ inhibitor, to the subject. Conversely, administration of a PI3K-p110δ inhibitor, or pharmaceutical composition comprising a PI3K-p110δ inhibitor, may be withheld from a subject in which wild-type or elevated PTEN protein activity and/or expression is detected.

According to this aspect, this disclosure provides for the use of a PI3K-p110δ inhibitor, or pharmaceutical composition comprising a PI3K-p110δ inhibitor, in the manufacture of a medicament for the treatment of an autoimmune disease or disorder in a subject expressing reduced or absent PTEN and/or SHIP-1. This aspect also provides a PI3K-p110δ inhibitor, or pharmaceutical composition comprising a PI3K-p110δ inhibitor, for use in the treatment of an autoimmune disease or disorder in a subject expressing reduced or absent PTEN and/or SHIP-1.

Combination Therapy

In the therapeutic methods of this disclosure, the PI3K-p110δ inhibitor compounds may be employed alone or in combination with other therapeutic agents for the treatment of an autoimmune disease or disorder, such as Type 1 Diabetes, SLE, or autoimmune thyroiditis. In these methods, a PI3K-p110δ inhibitor compound is combined in a pharmaceutical combination formulation, or dosing regimen as combination therapy, with a second therapeutic compound that has anti-inflammatory or immune suppressing properties or is otherwise useful for treating an autoimmune disease or symptoms thereof. For example, the second therapeutic agent may be a non-steroidal anti-inflammatory agent, or an antidiabetic agent. The second compound of the pharmaceutical combination formulation or dosing regimen preferably has complementary activities to the PI3K-p110δ inhibitor such that they do not adversely affect each other. Such compounds are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

Suitable dosages for any of the above coadministered agents are those described herein for the PI3K-p110δ inhibitor, such as idelalisib, and may be lowered due to the combined action (synergy) of the second identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternating therapy, a synergistic effect may be attained when the compounds are administered or delivered sequentially, e.g., by different injections in separate syringes, separate tablets or capsules, or separate infusions. In general, during alternating therapy, an effective dosage of each active ingredient is administered sequentially, i.e., serially, whereas in combination therapy, effective dosages of two or more active ingredients are administered together.

Pharmaceutical Formulations

The PI3K-p110δ inhibitor can be formulated according to known methods to prepare pharmaceutically useful compositions, whereby the PI3K-p110δ inhibitor is combined in a mixture with a pharmaceutically suitable excipient. Suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Additional pharmaceutical methods may be employed to control the duration of action of the PI3K-p110δ inhibitor. Controlled release preparations can be prepared through the use of polymers to complex or adsorb the PI3K-p110δ inhibitor.

In order to use a PI3K-p110δ inhibitor compound for the therapeutic treatment (including prophylactic treatment) of mammals, it is normally formulated in accordance with standard pharmaceutical practice as a pharmaceutical composition. Thus, this disclosure provides a pharmaceutical composition comprising a PI3K-p110δ inhibitor in association with a pharmaceutically acceptable diluent or carrier.

A typical formulation is prepared by mixing a PI3K-p110δ inhibitor compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the PI3K-p110δ inhibitor compound is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The PI3K-p110δ inhibitor compound is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Exemplary oral dosage formulations of PI3K-p110δ inhibitors, useful in practicing the therapeutic methods of this disclosure, include at least one PI3K-p110δ inhibitor, such as idelalisib, in an amount that is convenient and accurate for administration of the surprisingly low doses that the inventors have discovered to be efficacious in treating an autoimmune disease or disorder. Thus, exemplary oral dosage formulations of this disclosure may include tablets or capsules containing idelalisib ((S)-5-fluoro-3-phenyl-2-[1-(9H-purin-6-ylamino)-propyl]-3H-quinazolin-4-one) or a pharmaceutically acceptable salt thereof, in an amount between 5 mg and 25 mg, and at least one pharmaceutically acceptable excipient. Such tablet or capsule may contain 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, or 25 mg of idelalisib.

Articles of Manufacture

In another aspect of this disclosure, an article of manufacture, or "kit", containing materials useful for the treatment of autoimmune diseases and disorders in the methods described above is provided. The kit may include a container comprising a compound of PI3K-p110δ inhibitor. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a PI3K-p110δ inhibitor or a formulation thereof which is effective for treating the autoimmune disease or disorder. At least one active agent in the composition is a PI3K-p110δ inhibitor compound. The kit may further comprise directions for the administration of the PI3K-p110δ inhibitor compound and, if present, a second pharmaceutical formulation. For example, if the kit comprises a first composition comprising a PI3K-p110δ inhibitor compound and a second pharmaceutical formulation, the kit may further comprise directions for the simultaneous, sequential or separate administration of the first and second pharmaceutical compositions to a patient in need thereof.

These kits may be suitable for the delivery of solid oral forms of a PI3K-p110δ inhibitor compound, such as tablets or capsules. Such a kit preferably includes a number of unit dosages and may further include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

The following examples are intended to be purely exemplary and should not be considered to be limiting in any way.

EXAMPLES

The following methods were used to conduct the experiments described in Examples 1-7, below:

Mice:

Except where otherwise indicated, 6-16 week old mice were used in all experiments. Both male and female mice were used, but experiments were sex matched and both sexes gave identical results, with the exception of only female mice being used in the VH125.NOD experiments as female mice develop accelerated disease. hCD20-TamCre animals (Khalil, et al. Science 336: 1178-81) were intercrossed with mice carrying the rosa26-flox-STOP-YFP allele (Srinivas, et al., BMC Dev. Biol. 1:4), generating mice in which YFP is expressed in B cells upon Cre activation. These mice were crossed with Ars/A1 (Benschop, et al., Immunity 14: 33-43) transgenic mice to generate hCD20-TamCre×rosa26-flox-STOP-YFP×Ars/A1 mice. B cells from these mice will be referred to as WT Ars/A1. These mice were also crossed with SHIP-1$^{flox/flox}$ mice (Karlsson, et al. J Exp Med 198: 333-40). hCD20-TamCre×rosa26-flox-STOP-YFP×Ars/A1 mice were also crossed to PTEN$^{flox/flox}$ mice (Anzelon, et al., Nat Immunol 4: 287-94) and SHP-1$^{flox/flox}$ mice to generate mice in which SHIP-1, PTEN and SHP-1 deletion can be induced in anergic B cells. hCD20-TamCre×rosa26-flox-STOP-YFP×PTEN$^{flox/flox}$×Ars/A1 were crossed to hCD20-TamCre×rosa26-flox-STOP-YFP×SHIP-1$^{flox/flox}$×Ars/A1 to generate hCD20-TamCre×rosa26-flox-STOP-YFP× PTEN$^{flox/wt}$× SHIP-1$^{flox/wt}$×Ars/A1 to allow for the double haploinsufficiency of both PTEN and SHIP-1 within B cells.

Adoptive Transfers and Tamoxifen Induction:

2 hours before adoptive transfer, C57BL/6 recipient mice received 200 rads irradiation. For MD4 transfers, recipients did not receive prior irradiation. B cells from donor mice were isolated via depletion of CD43+ cells with anti-CD43-conjugated magnetic beads (MACS anti-mouse CD43; Miltenyi Biotec). Alternatively, CD4+ T cells were isolated via CD4 positive selection (MACS anti-mouse CD4 (L3T4) Miltenyi Biotec). Resultant populations were >97% pure based on flow cytometric analyses. Donor B cells were labeled with either CellTrace Violet (Molecular Probes) or CFSE (Molecular Probes) at 5 μM for 5 minutes at room temperature prior to transfer. Donor CD4 T cells were labeled with CFSE (Molecular Probes) at 5 μM for 5 minutes at room temperature prior to transfer. 1-2×10$^6$ donor cells in 200 μl PBS were adoptively transferred via IV injection. 24 hours post transfer, tamoxifen was administered to activate Cre. Tamoxifen (Sigma-Aldrich) was dissolved in 100% corn oil (Sigma-Aldrich) at 20 mg/ml. Recipient mice were injected IP with 100 μl (2 mg) on two consecutive days.

Manufacturing and Administration of Idelalisib Containing Rodent Chow:

Idelalisib (LC Laboratories) was shipped to ResearchDiets Inc. for blending the compound homogenously into modified OSD with 24 kcal % protein, 16 kcal % fat, 60% kcal % carbohydrate, 100 g of cellulose and 25 g inulin. Diet dose (DD) is calculated by multiplying the single daily dose (SD) by the body weight of a mouse (BW) and dividing that by the daily food intake (FI) [DD=(SD×BW)/FI]. Chow used includes base chow as described above with: +0 mg idelalisib/kg diet (Vehicle Control), +600 mg idelalisib/kg diet (30 mg/kg ingested idelalisib dose), +75 mg idelalisib/kg diet (3.75 mg/kg ingested idelalisib dose), and +18.75 mg idelalisib/kg diet (0.9375 mg/kg ingested idelalisib dose).

For PTEN$^{fl/wt}$×SHIP-1$^{fl/wt}$ and SHP-1$^{fl/fl}$ adoptive transfers, control chow and idelalisib containing chow was given to mice on day 7 post-tamoxifen administration. For MD4 and OT-II adoptive transfers, control chow and idelalisib containing chow was given to mice 2 days post transfer. For VH125.NOD experiments animals are placed on control chow immediately after weaning. Following 2 consecutive diabetic blood glucose readings (between 150-200 mg/dl) animals either remain on vehicle control chow or are placed on 0.9375 mg/kg idelalisib containing chow and disease progression is monitored. For NP$_4$Ova-alum experiments, animals were placed on either vehicle control chow or 0.9375 mg/kg idelalisib chow for 28 days and subsequently immunized.

Antigens and Immunization:

HEL conjugated to SRBCs was used to produce antigen for experiments with MD4 B cells. SRBCs (Colorado Serum Company) were stored in Alsever's solution at 4° C. SRBCs are washed 3 times in PBS prior to use. 1 ml of 50 mg/ml of the chemical crosslinker N-(3-Dimethylaminopropyl)-N-ethylcarbodiimide hydrochloride (Sigma-Aldrich) was added to 1 ml packed SRBCs and 15 ml of 5 mg/ml HEL (Sigma-Aldrich), mixed and rotated at room temperature for 45 minutes. Mice were immunized IP with 200 μl of a 5% HEL-SRBC in PBS. For NP$_4$Ova-Alum immunizations, 10 mg/ml alum and 5 mg/ml NP$_4$Ova were mixed to a final concentration of 250 μg/ml NP$_4$Ova and 2.5 mg/ml alum and rotated for 3 hours at room temperature. NOD mice were placed either on vehicle control chow or 0.9375 mg/kg idelalisib chow for 28 days. Mice were then immunized with NP$_4$Ova-alum IP in 200 μl/mouse, and responses were measured on day 7 and day 14 post-immunization.

Phenotypic Analysis by FACS:

Spleens were mechanically disrupted, single-cell suspensions were generated, and red blood cells were lysed with ammonium chloride TRIS. Cells were resuspended in PBS containing 1% FBS and incubated with indicated antibodies. For analysis of cell surface markers, antibodies against the following molecules were used: B220-PE (BioLegend), B220-BV786 (BD Biosciences), B220-BV510 (BioLegend), CD4-BV711 (BioLegend), CD8-BV421 (BioLegend), CD138-PECy7 (BioLegend), CD69-BV786 (BD Biosciences), CD86-PerCPCy5.5 (BioLegend). After cell surface staining, the cells were fixed and permeabilized with Cytofix/Cytoperm (BD) per manufacturer's instructions and stained with Dylight650-E4 anti-Ars/A1 idiotype (produced and conjugated in our laboratory) OR HEL-650 (produced and conjugated in our laboratory) and Alexa Fluor 488-anti-GFP (rabbit polyclonal; Life Technologies). Events were collected on a CyAn ADP (Dako) and subsequent analysis using FlowJo software (Tree Star).

Analysis of Calcium Mobilization:

For measurements of intracellular free calcium concentration ($[Ca^{2+}]_i$), RBC-depleted single-cell suspended splenocytes were simultaneously stained with CD8-PE (BD Biosciences), CD4-APC (BioLegend) or B220-PE and loaded with Indo-1 acetoxymethyl (Molecular Probes), as described previously (Gauld, et al., Nat Immunol 6: 1160-1167). For analysis of ($[Ca^{2+}]_i$), cells were suspended at $10 \times 10^6$ cells/ml in warm IMDM+2% FBS in a 500 ul volume. Cells were acquired for 30 seconds to establish a baseline, and then stimulated with 5 µg/ml of F(ab')$_2$ rabbit anti-mouse anti-IgG (H&L; Invitrogen)+/− indicated doses of idelalisib and acquired for 3 minutes. For CD4 and CD8 T cells, cells were acquired for 30 seconds to establish a baseline, and then 10 µg/ml of anti-CD3-biotin (BD Biosciences)+/− indicated doses of idelalisib was added, 60 seconds later 20 µg/ml streptavidin (Sigma-Aldrich) was added and acquired for 3 minutes. Mean relative ($[Ca^{2+}]_i$) was monitored over time using an LSR Fortessa X-20 (BD) with analysis using FlowJo software.

Analysis of Phosphorylated Signaling Intermediaries:

RBC-depleted single-cell suspended splenocytes were suspended at $10 \times 10^6$ cells/ml in serum free IMDM, +/− indicated doses of idelalisib (as indicated in FIG. 4) and rested for 1 hour at 37° C. Cells are then washed 2× in serum free IMDM, and stimulated with 5 µg/ml of F(ab')$_2$ rabbit anti-mouse anti-IgG (H&L; Invitrogen) or 10 µg/ml anti-CD3-biotin (BD Biosciences)+20 µg/ml streptavidin (Sigma-Aldrich) for 2 minutes. Signaling was stopped by addition of 20% PFA to a final concentration of 2%, incubated at 37° C. for 15 minutes and resuspended in 100% ice-cold MeOH (directly from −80° C.). Cells were then placed on ice for 30 minutes and placed at −20° C. for storage. For analysis, cells were stained with B220-BV786, CD4-BV711, CD8-BV421, and/or pAKT-Alexa Fluor 647 (BD Biosciences), pPLCγ-PE (BD Biosciences), pBTK-BV421 (BD Biosciences) pSyk/Zap70-PE (BD Biosciences) at room temperature for 1 hour. Cells were washed 3 times and samples were acquired in triplicate on an LSR Fortessa X-20 (BD) with analysis using FlowJo software.

Enzyme Linked Immunosorbent Assay:

For detection of IgM$^a$ anti-Ars antibodies, microtiter plates were coated with 10 µg/ml Ars-BSA16 in PBS and blocked with 2 mg/ml BSA in PBS 0.05% Tween-20. For detection of IgM$^a$ anti-HEL antibodies, microtiter plates were coated with 10 µg/ml HEL in PBS and blocked with 2 mg/ml BSA in PBS 0.05% Tween-20. For detection of total NP-specific IgM and IgG, microtiter plates were coated with 20 µg/ml NP27BSA and blocked with 2 mg/ml BSA in PBS 0.05% Tween-20. Serial dilutions of mouse serum in PBS were added and incubated overnight at 4° C. Ars/A1-derived IgM$^a$ antibodies and MD4-derived HEL IgM$^a$ antibodies were detected with biotinylated DS.1 anti-IgM$^a$ (BD Pharmingen) in PBS, followed by Streptavidin-HRP (Thermo Fisher Scientific). For NP-specific IgM antibodies were detected using goat-anti-mouse IgM-HRP (SouthernBiotech). For NP-specific IgG antibodies were detected using goat-anti-mouse IgG-HRP (SouthernBiotech). Between all steps, plates were washed 3 times with PBS 0.05% Tween-20. The ELISA was developed with TMB single solution (Invitrogen) and the reaction was stopped with 1M HCl. OD was measured at 450 nm using a VERSAMax plate reader (Molecular Devices) and data analyzed with SoftMax Pro6 software.

ELISPOT:

For detection of IgM$^a$ anti-Ars antibodies, microtiter plates were coated with 10 µg/ml Ars-BSA16 in PBS and blocked with 2 mg/ml BSA in PBS 0.05% Tween-20. For detection of IgM$^a$ anti-HEL antibodies, microtiter plates were coated with 10 µg/ml HEL in PBS and blocked with 2 mg/ml BSA in PBS 0.05% Tween-20. For detection of total NP-specific IgM and IgG, microtiter plates were coated with 20 µg/ml NP$_{27}$BSA and blocked with 2 mg/ml BSA in PBS 0.05% Tween-20. For detection of high affinity NP-specific IgM and IgG, microtiter plates were coated with 20 µg/ml NP$_2$BSA and blocked with 2 mg/ml BSA in PBS 0.05% Tween-20. Plates were washed 3 times prior to use with PBS 0.05% Tween-20. RBC-depleted single-cell suspension of splenocytes in complete medium were added in two-fold serial dilutions starting at $1/100^{th}$ of a spleen in the first well. Plates were incubated overnight at 37° C. Ars/A1-derived IgM$^a$ antibodies and MD4-derived HEL IgM$^a$ antibodies were detected with biotinylated DS.1 anti-IgM$^a$ (BD Pharmingen) in PBS, followed by Streptavidin-AP (SouthernBiotech). For NP-specific IgM antibodies were detected using goat-anti-mouse IgM-AP (SouthernBiotech). For NP-specific IgG antibodies were detected using goat-anti-mouse IgG-AP (SouthernBiotech). Between all steps, plates were washed 3 times with PBS 0.05% Tween-20. The plates were developed by incubated with ELISPOT developing buffer (25 µm 5-bromochloro-3-indolyl phosphate p-toluidine, 100 nm NaCl, 100 mM Tris, and 10 mM MgCl$_2$, pH 9.5) for 1 hour. The reaction was stopped by washing the plates 3 times with PBS 0.05% Tween-20. The number of spots at a cell dilution in the linear range was determined, and the number of ASCs was calculated.

Statistics:

Data were analyzed using Prism GraphPad Software. Statistical analyses were performed using the indicated statistical tests in the brief description of the figures. P values 0.05 were considered statistically significant. Throughout the figures, asterisks are used to denote p-values of: *=p≤0.05, =p≤0.01, *=p≤0.005 and ****=p≤0.0001.

Example 1

Idelalisib Prevents T1D Progression in VH125.NOD Mice

The inventors' began exploring the ability of low doses of p110δ inhibitor to arrest progression of T1D in a genetically complex model of autoimmunity. The most commonly used mouse model of T1D, the non-obese diabetic mouse, reflects disease progression in the human. Female NOD mice develop overt diabetes at 20 weeks of age, with lymphocytic infiltration of the islets and autoantibody production preceding hyperglycemia and diabetes. NOD mice are protected from disease development upon deletion of the B cell compartment (NOD.uMT$^{-/-}$), or upon skewing of the BCR repertoire away from insulin reactivity (VH281.NOD), but not upon removal of autoantibody (mIgM NOD). In these studies the inventors utilized the VH125.NOD mouse model of disease in which mice carry an immunoglobulin heavy chain transgene specific for insulin, the dominant autoantigen in T1D. Importantly, the transgenic heavy chain can pair with any endogenous light chain, resulting in a frequency of peripheral B cells reactive with insulin of 1-3%. In WT female NOD mice, disease penetrance only reaches 70%, but skewing of the B cell repertoire towards insulin reactivity leads to 100% penetrance of disease in female mice and earlier disease onset.

While multiple insulin-dependent (Type 1) diabetes (Idd) loci contribute to disease development in NODs, B cells in these mice exhibit a marked reduction in PTEN levels in both insulin-reactive B cells and total B cells compared to closely related, autoimmunity resistant VH125.C57BL/6-H2g7 mice. On this background, but not VH125.NOD, high affinity insulin-reactive B cells are anergic. NOD mice have increased susceptibility to additional autoimmune diseases, such as Rheumatoid Arthritis (RA), SLE and the Experimental Autoimmune Encephalomyelitis (EAE) mouse model of MS. Reduced B cell expression of PTEN has been reported in lupus patients, and the inventors have observed reduced PTEN levels in the B cells of both T1D and AITD patients. Thus, loss of B cell tolerance in both man and mouse may be driven in part by PI3K pathway dysregulation. We therefore postulated VH125.NOD mice and T1D patients, both of which have PI3K pathway regulation defects, may benefit from low dose idelalisib, a p110δ inhibitor, to reinstate anergy of autoreactive B cells.

Figure 1B:
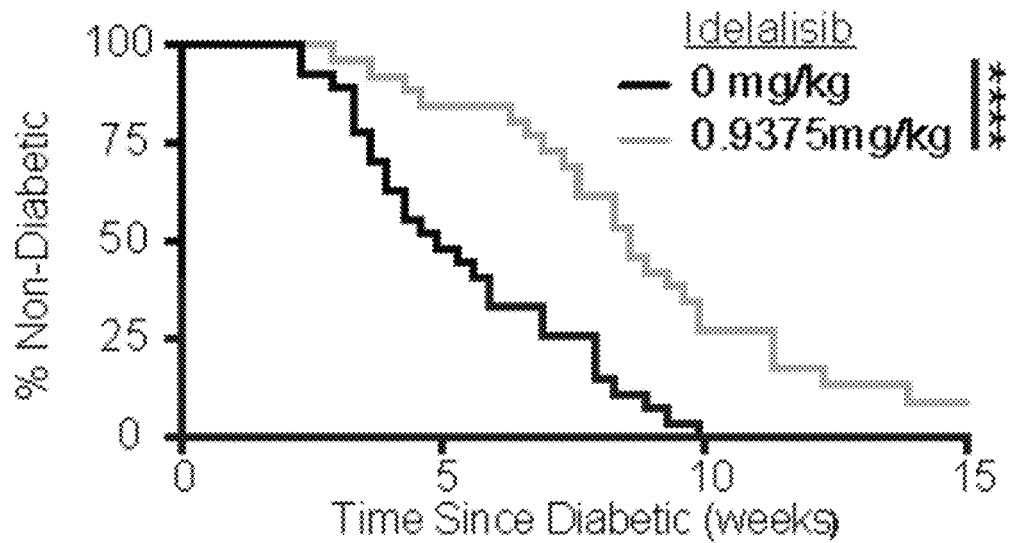

To test this possibility, immediately post-weaning, female VH125.NOD mice were placed on vehicle control chow to allow habituation to the diet. Upon two consecutive blood glucose readings in the pre-diabetic range, some mice were maintained on the vehicle control chow, while others were fed 0.9375 mg/kg idelalisib containing chow (FIG. 1A). Disease progression was monitored based on blood glucose levels and visible signs of disease (i.e., hunching, scruffy fur, excessive urination). In mice receiving 0.9375 mg/kg idelalisib, disease progression was significantly delayed, and survival was extended (FIG. 1B).

Example 2

NOD Mice on Low-Dose Idelalisib Treatment Remain Immunocompetent

Figure 1C:
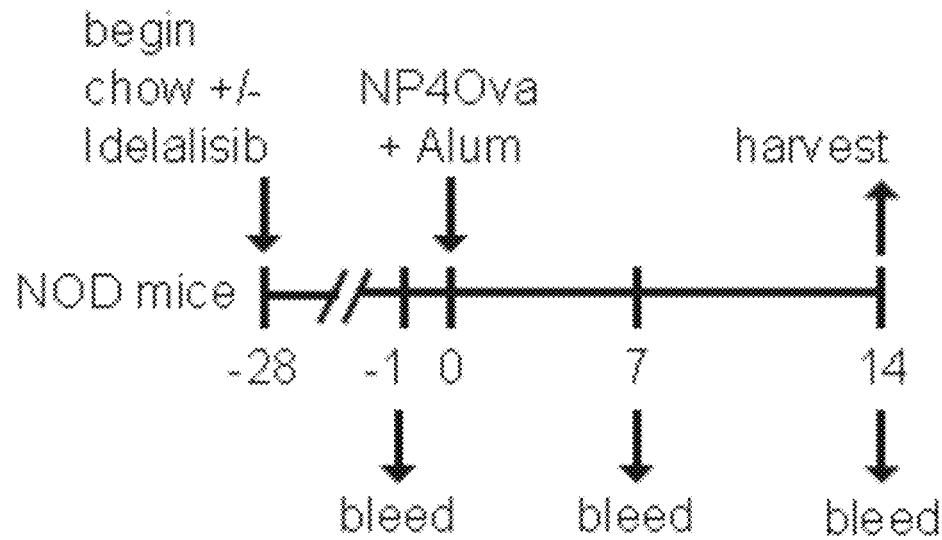
Figure 1D:
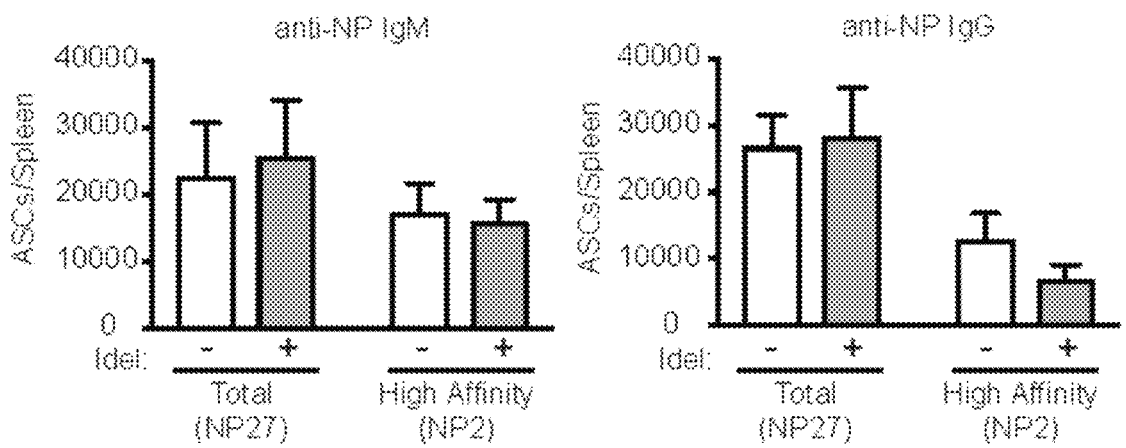
Figure 1E:
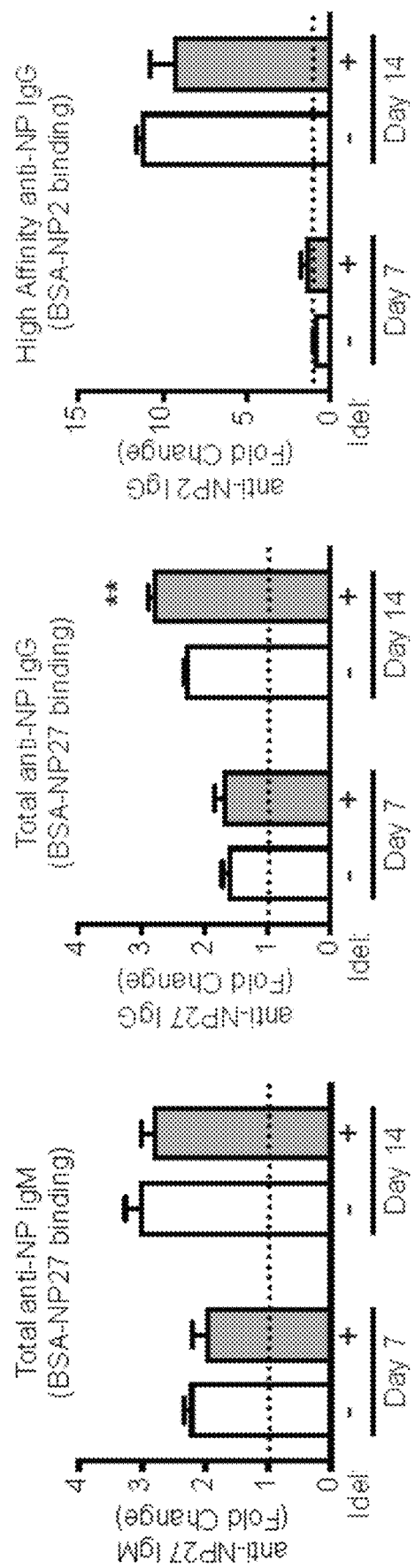

B cell depletion therapies are somewhat efficacious in T1D, but are not without safety concerns. Removal of an arm of the adaptive immune system can leave patients susceptible to infection and prevent proper response to immunization. The inventors therefore sought to determine if low dose idelalisib treatment would spare responsiveness to immunization. Non-diabetic female NOD mice were placed on vehicle control or 0.9375 mg/kg idelalisib containing chow for 4 weeks, immunized with NP4Ova+Alum, and their antibody response assessed (FIG. 1C). 14 days post-immunization, the anti-NP IgM response in the spleen was not different between the vehicle control and 0.9375 mg/kg idelalisib-treated cohorts. Further, the number of total anti-NP IgM antibody secreting cells (ASCs) per spleen was equivalent, as were the number of high-affinity IgM anti-NP ASCs/spleen (FIG. 1D, left panel). There was no observed difference between the vehicle control and 0.9375 mg/kg idelalisib treated cohorts in either total IgG anti-NP or high affinity IgG anti-NP ASCs/spleen (FIG. 1D, right panel). The levels of IgM anti-NP and IgG anti-NP found in the periphery was also equivalent (FIG. 1E). There was no difference in B cell numbers in the spleens of animals receiving vehicle control and 0.9375 mg/kg idelalisib containing chow. These data show low dose idelalisib treatment does not affect the ability to respond to immunization, as evidenced by equivalent levels of class switching and affinity maturation between the treated and untreated groups. Thus, animals receiving doses of idelalisib sufficient to slow progression of disease and prolong survival in VH125.NOD mice remain immunocompetent, alleviating potential adverse outcomes inherently associated with B cell-depleting therapies.

Example 3

Autoreactive PTEN$^{-/+}$×SHIP-1$^{-/+}$ B Cells Re-Establish Anergy when Treated with Idelalisib The inventors next sought to confirm the specificity of the idelalisib effect for autoimmunity driven by dysregulation of the PI3K pathway. Regulation of the PI3K pathway by the inositol phosphatases PTEN and SHIP-1 is required for maintenance of B cell anergy. B cells in T1D, AITD, and SLE patients express reduced PTEN and SHIP-1, presumably due to an increase in the miRNAs that regulate them, e.g. mir-7 and mir-155. Studies in animal models utilizing B cell targeted conditional deletion of either of these molecules is sufficient to drive autoreactive B cells out of anergy leading to rapid proliferation and differentiation into antibody secreting cells. Removal of a single allele of both PTEN and SHIP-1 is also sufficient to allow for loss of anergy because both degrade PI(3,4,5)P3. To best approximate physiologic conditions, the inventors utilized B cell-targeted conditional deletion (huCD20cre$^{tam}$) of one allele of PTEN (PTEN$^{flox/+}$) and one allele of SHIP-1 (SHIP-1$^{flox/+}$), coupled with a YFP-reporter to determine cre-activity, and crossed onto an anti-DNA (Ars/A1) transgenic background that renders B cells anergic (as described above).

Figure 2A:
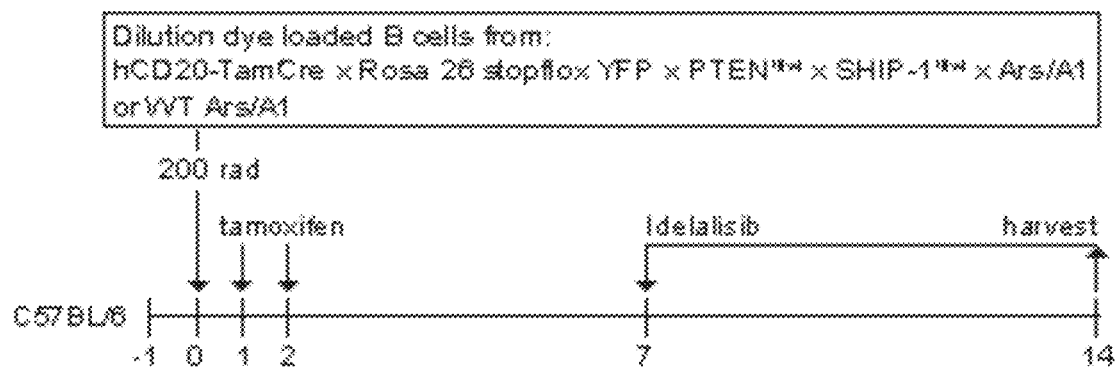
FIGS. 2A-2H show autoreactive PTEN$^{fl/wt}$×SHIP-1$^{-/-}$ B cells re-establish anergy when treated with idelalisib.
Figure 2B:
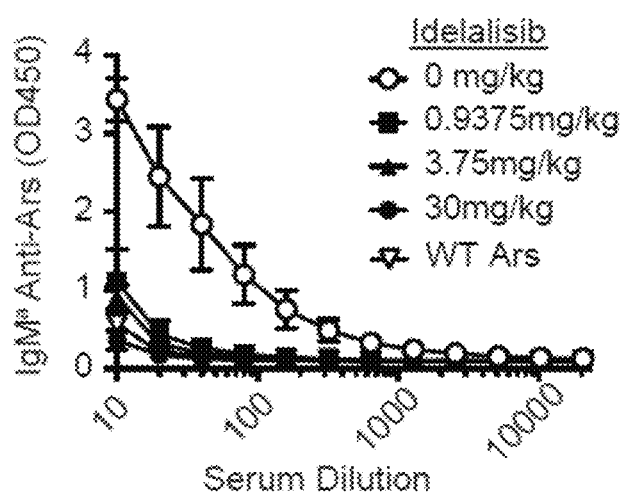
Figure 2C:
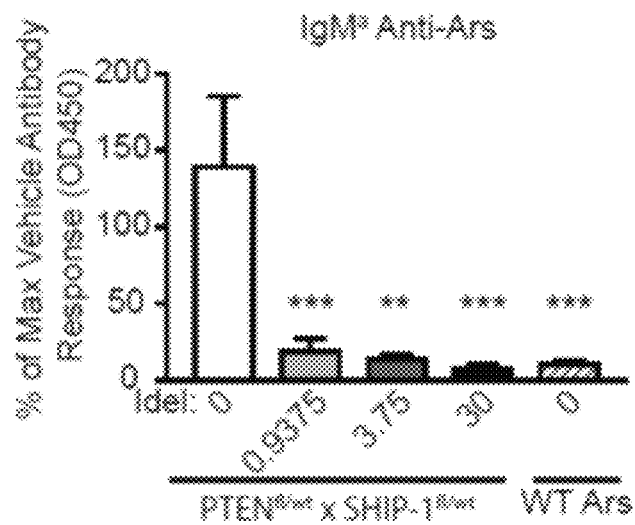
Figure 2D:
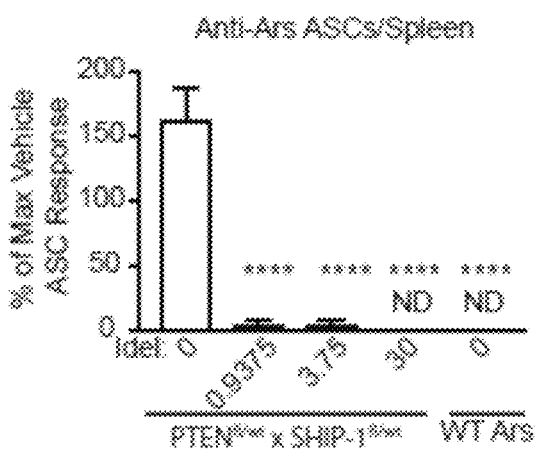
Figure 2F:
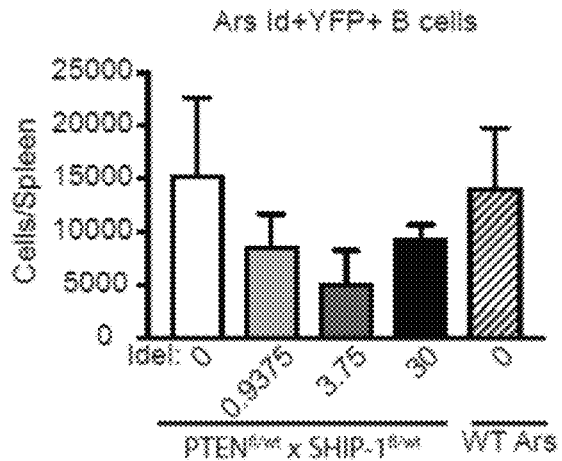
Figure 2E:
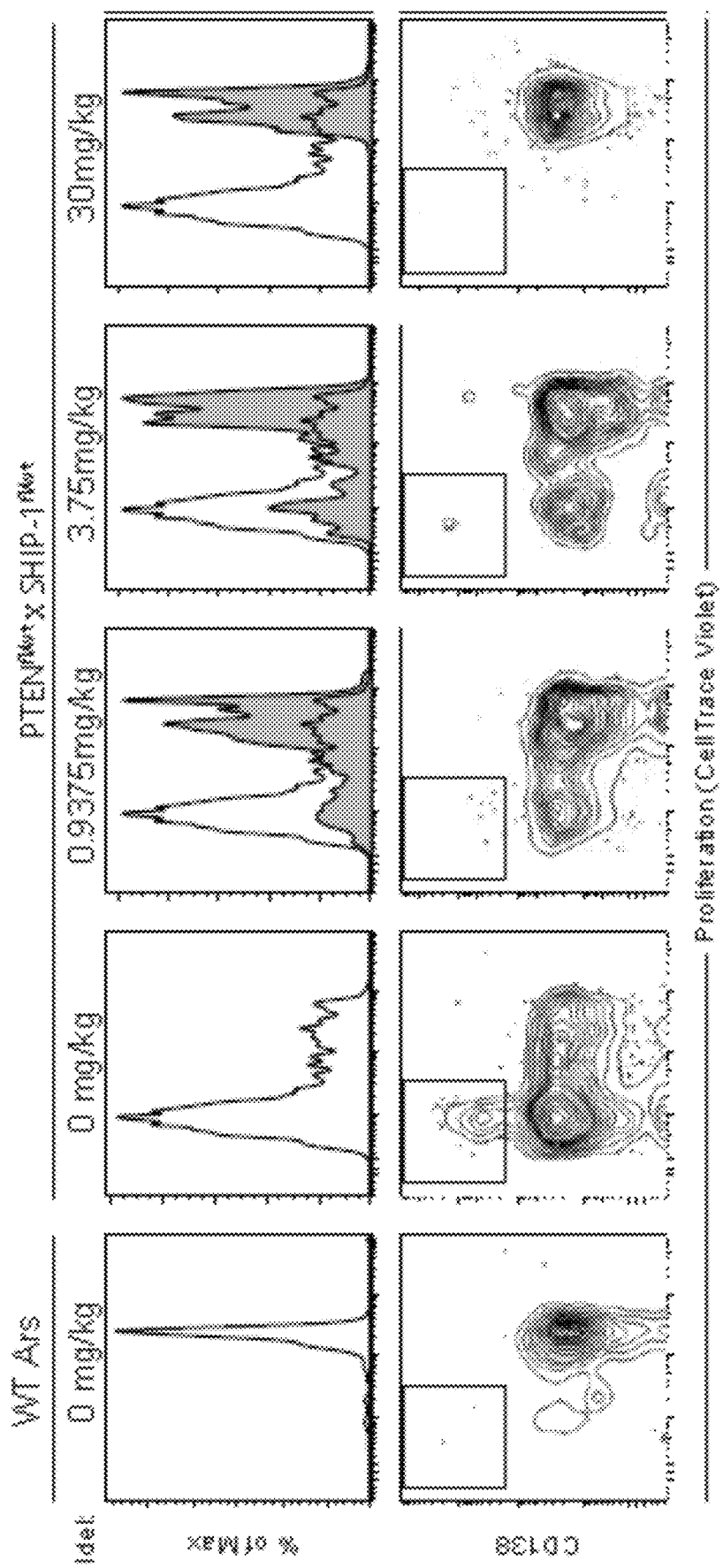
Figure 2G:
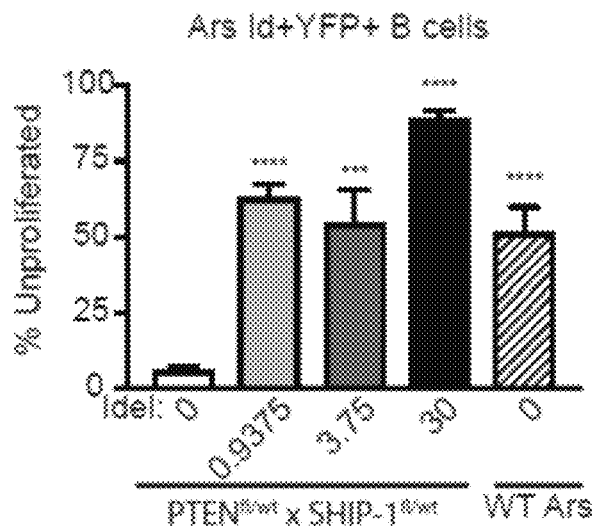
Figure 2H:
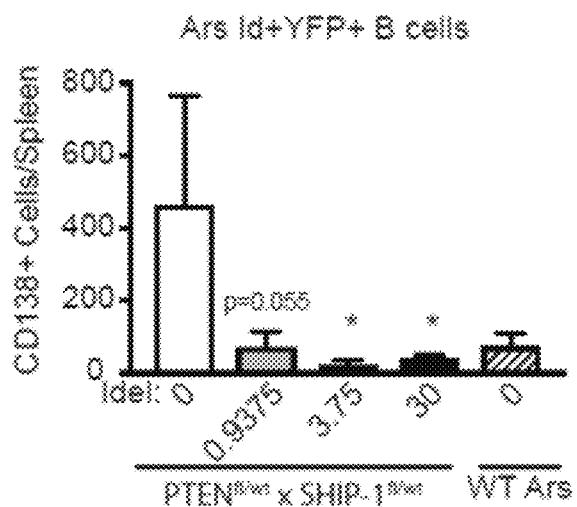

Anergic B cells were adoptively transferred into C57BL/6 recipients as shown diagrammatically in FIG. 2A. Seven days post tamoxifen treatment, anergy was lost and idelalisib treatment was begun. Fourteen days post adoptive transfer, mice on 0.9375 mg/kg, 3.75 mg/kg, and the clinically-prescribed dose of 30 mg/kg of idelalisib-containing chow had significantly decreased serum autoantibody relative to untreated controls (FIG. 2B, quantified FIG. 2C). Furthermore, the number of autoreactive ASCs/spleen was significantly reduced in cohorts receiving 0.9375 mg/kg and 3.75 mg/kg idelalisib containing chow, with undetected ASCs in cohorts receiving 30 mg/kg idelalisib containing chow (FIG. 2D). The reduction in peripheral autoantibody, as well as ASCs/spleen was not due to a differential recovery of transferred cells among treatment groups, as no significant difference in total Ars/A1 idiotype+ YFP+ B cells in the spleens of animals at day 14 post transfer was found, regardless of treatment (FIG. 2F). Adoptively transferred PTEN$^{-/+}$×SHIP-1$^{-/+}$ B cells from cohorts receiving tamoxifen and 0.9375 mg/kg, 3.75 mg/kg, and 30 mg/kg idelalisib-containing chow underwent significantly decreased proliferation (FIG. 2E top panel, quantified FIG. 2G), and plasmablast differentiation as measured by CD138 positivity (FIG. 2E bottom panel, quantified FIG. 2H) relative to mice receiving vehicle control chow. These data demonstrate that 0.9375 mg/kg idelalisib, as well as higher doses, is sufficient to constrain an autoreactive B cell response driven by haploinsufficiency of the inositol phosphatases that regulate the PI3K pathway.

Example 4

Autoreactive SHP-1$^{-/-}$ B Cells do not Maintain Anergy when Treated with Low Dose Idelalisib SHP-1 is a regulatory SH2-domain containing tyrosine phosphatase which mediates the function of inhibitory receptors such as CD22, PD1, and FCγRIIB, and is necessary for maintenance of B cell tolerance. Allelic variants of SHP-1 have been shown to increase risk of developing SLE, with studies indicating a subset of SLE patients having reduced SHP-1 protein in their B cells. Additionally, reductions in SHP-1 mRNA and protein have been observed in peripheral blood B cells of MS patients. Studies in viable motheaten mice have revealed that a mutation in a splice site in Ptpn6, the gene that encodes SHP-1, resulting in an 80-90% reduction in enzymatic activity, leads to severe B cell immunodeficiency and autoantibody production. Our laboratory has shown B cell-targeted conditional deletion of SHP-1 from anergic B cells in vivo leads to proliferation and autoantibody production. SHP-1 is required to maintain B cell anergy, acting through a pathway distinct from SHIP-1 and PTEN.

Figure 3A:
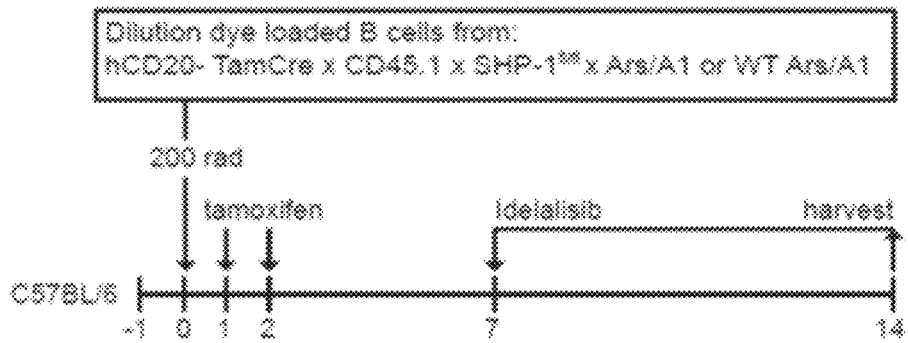
FIGS. 3A-3H show autoreactive SHP-1$^{-/-}$ B cells do not maintain anergy when treated with low dose idelalisib.
Figure 3B:
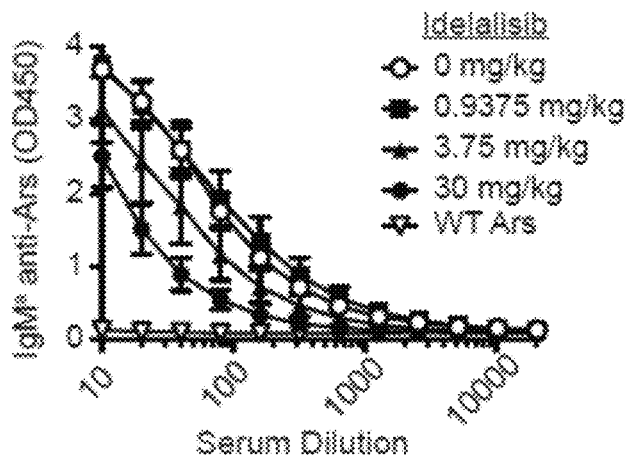
Figure 3C:
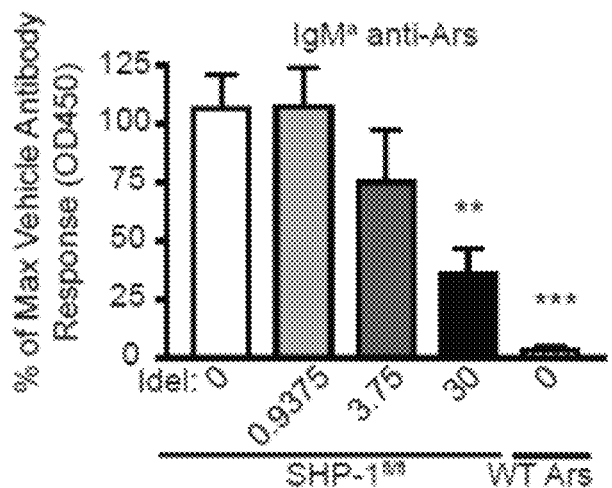
Figure 3D:
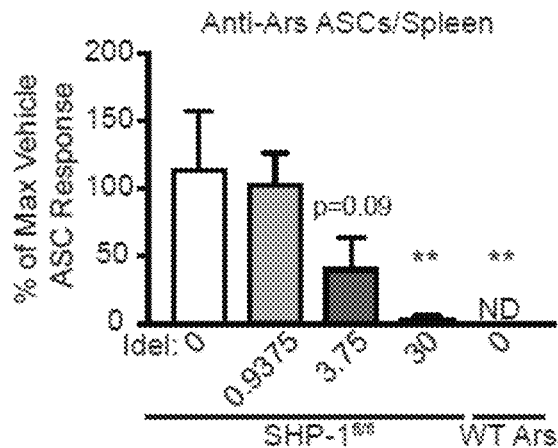
Figure 3E:
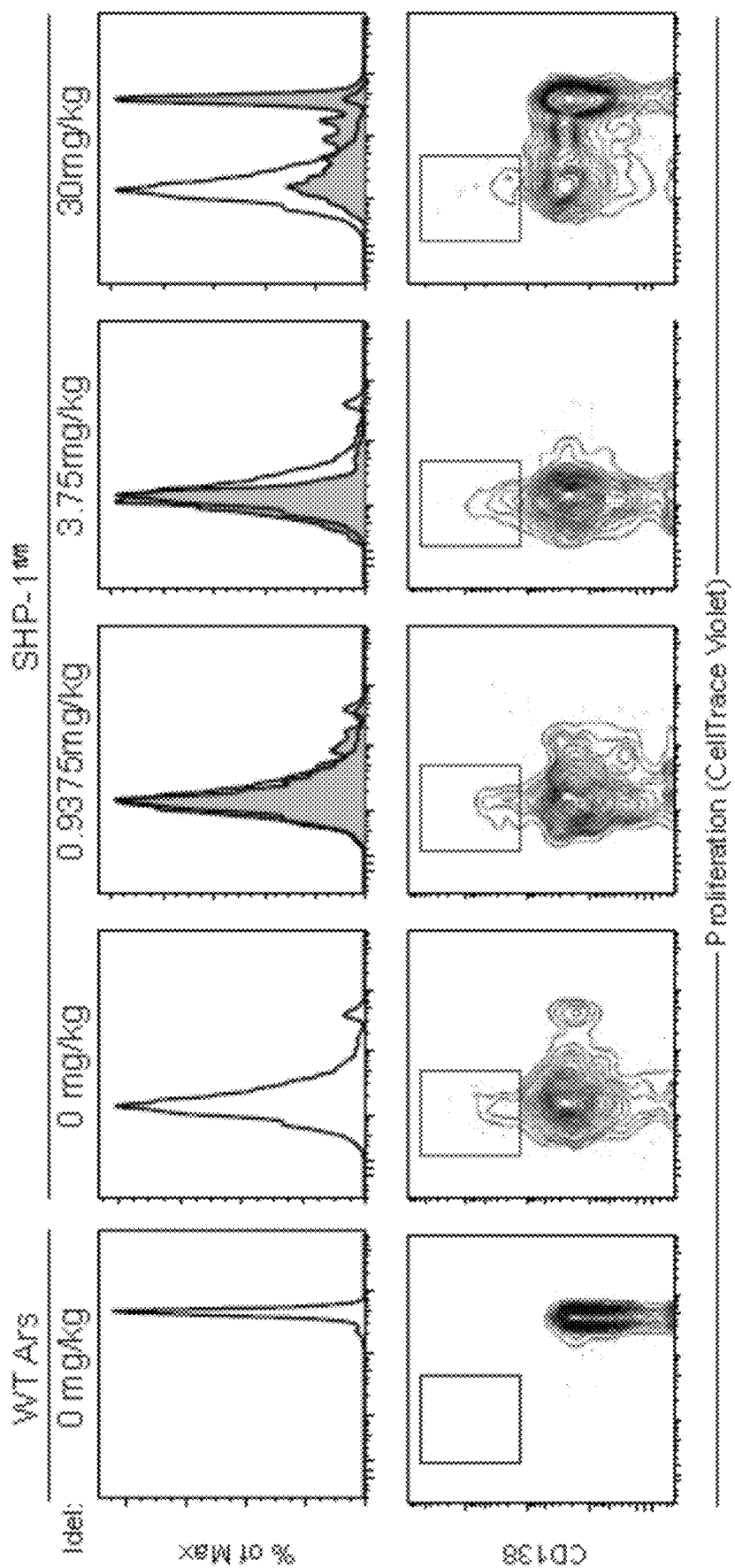
Figure 3F:
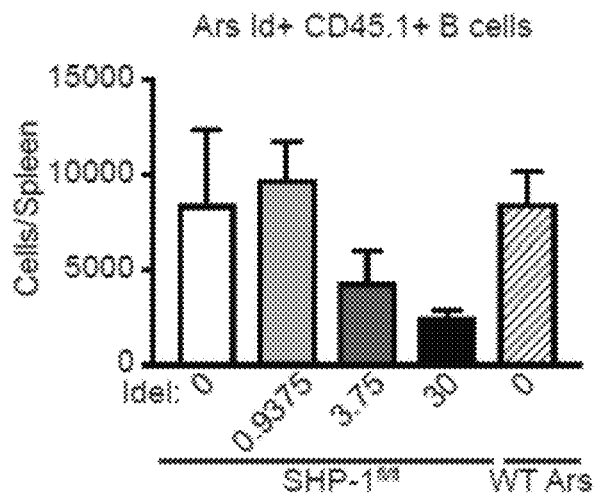
Figure 3G:
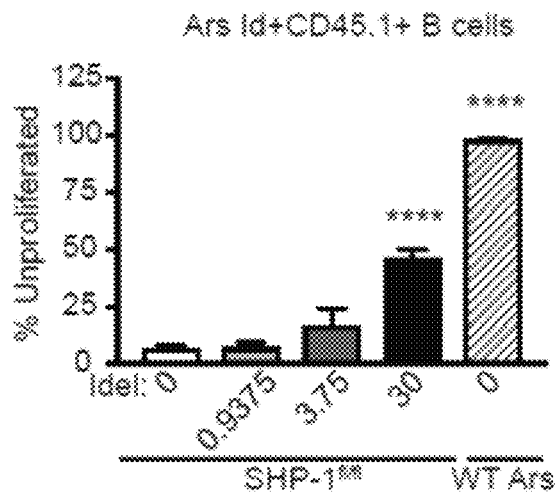
Figure 3H:
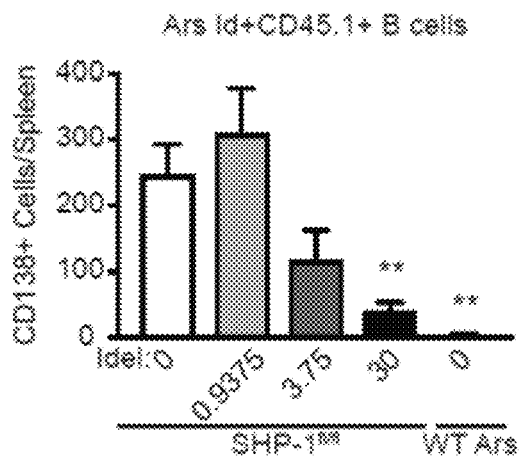

To test the specificity of idelalisib effects on non-PI3K pathway dysregulation-mediated autoimmunity we used the adoptive transfer system described in FIG. 3A in conjunction with SHP-1$^{flox/flox}$ B cells. Idelalisib-containing chow was administered at day 7 post transfer, upon removal of SHP-1 protein from transferred cells. Unlike its enforcement of anergy caused by PI3K pathway dysregulation, low and intermediate dose idelalisib treatment had no effect on loss of anergy caused by SHP-1 induced deficiency. However, autoimmunity was blocked by high dose idelalisib (FIG. 3B, quantified in FIGS. 3C and 3D). Although a trend of reduced recovery of adoptively transferred SHP-1-/- B cells from the spleens of animals receiving idelalisib-containing chow was observed, this was not significant (FIG. 3F). In animals receiving vehicle, 0.9375 mg/kg or 3.75 mg/kg idelalisib-containing chow, SHP-1$^{-/-}$ B cells proliferated (FIG. 3E top panel, quantified FIG. 3G) and differentiated (FIG. 3E bottom panel, quantified FIG. 3H) equivalent amounts. Only in animals receiving 30 mg/kg idelalisib-containing chow did SHP-1$^{-/-}$ B cells undergo decreased proliferation and differentiation (FIGS. 3E, 3G, and 3H). These findings demonstrate that the particular risk allele-mimetic conditions at play determine the ability of partial p110δ inhibition to enforce tolerance.

Example 5 p110δ Inhibition Suppresses BCR-Mediated Calcium Flux and Reduces Phosphorylation of its Downstream Signaling Intermediaries In naïve B cells, antigen receptor stimulation leads to phosphorylation of the two conserved tyrosines in the ITAMs of CD79a/b leading to recruitment of Lyn and Syk to the receptor complex. Lyn phosphorylates CD19, allowing its interaction with Lyn and PI3K and subsequent activation of p110δ. p110δ converts PI(4,5)P2 to PI(3,4,5) P3, generating docking sites for PH-domain containing downstream BCR effectors such as PLCγ, AKT, and BTK. Multiple parallel pathways emanate from this signalosome, ultimately leading to cell activation, differentiation, proliferation and migration.

Figure 4A:
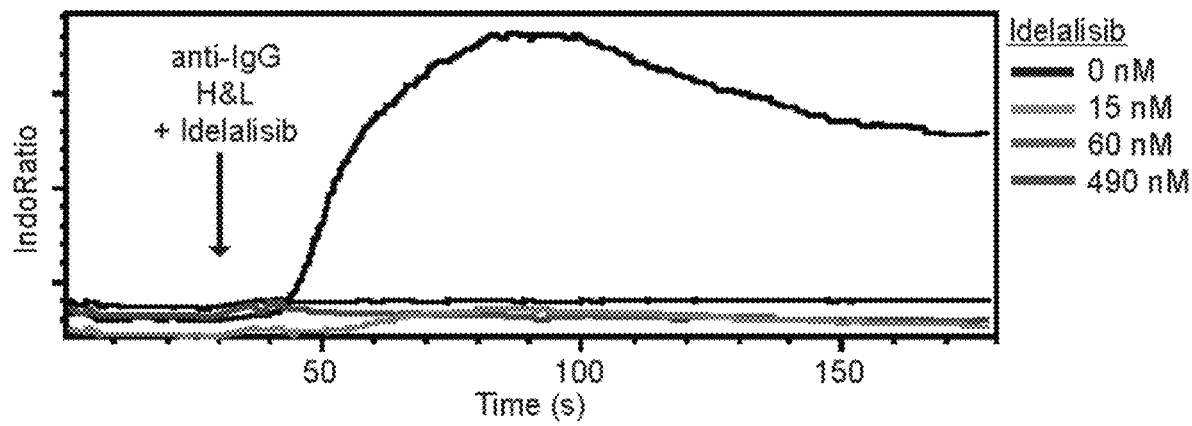
FIGS. 4A-4C show p110δ inhibition suppresses B cell calcium flux and reduces phosphorylation of downstream signaling intermediaries.
Figure 4B:
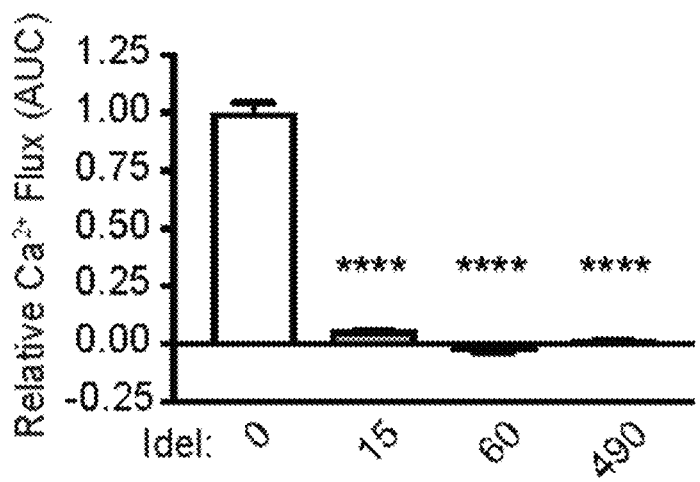
Figure 4C:
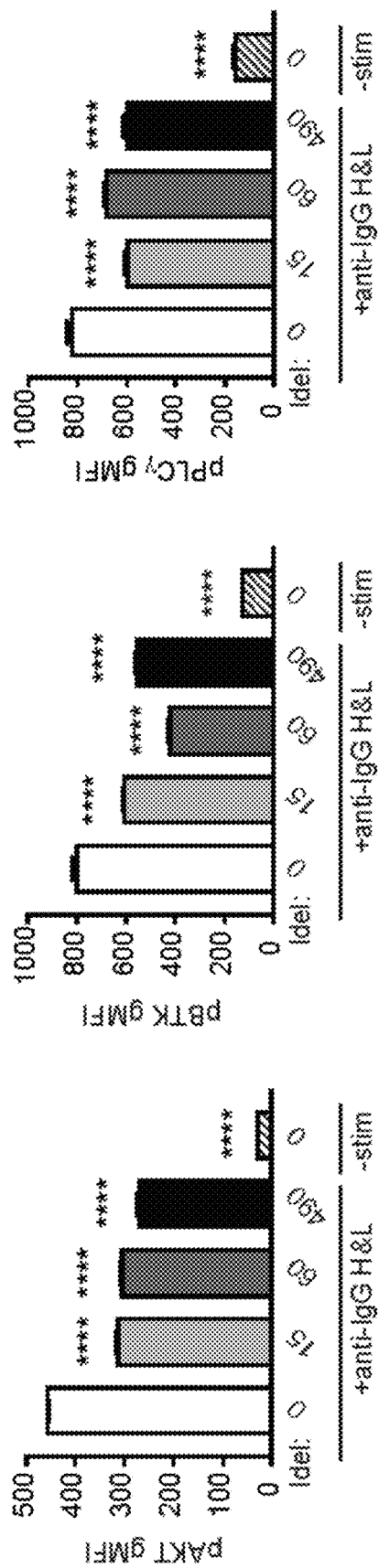

To determine whether p110δ inhibition blocks proximal BCR signaling events, the inventors stimulated splenic B cells from C57BL/6 mice with polyclonal F(ab')$_2$ anti-Ig heavy and light chain antibodies with simultaneous addition of 0 nM, 15 nM, 60 nM and 490 nM idelalisib. It is noteworthy that these are equivalent to doses of 0 mg/kg, 0.9375 mg/kg, 3.75 mg/kg and 30 mg/kg of idelalisib, respectively, used in vivo. All doses of idelalisib tested suppressed calcium mobilization (FIG. 4A, quantified FIG. 4B). Similarly, phosphorylation of AKT, BTK, and PLCγ are significantly reduced following exposure to all doses of inhibitor (FIG. 4C). These findings demonstrate that low doses of p110δ inhibitor that enforce anergy while sparing the antibody response have an inhibitory effect on early events in BCR signaling that are predicted to be dependent on PI3K activation.

Example 6

Dose-Dependent Idelalisib Inhibition of Antibody Responses

Figure 5A:
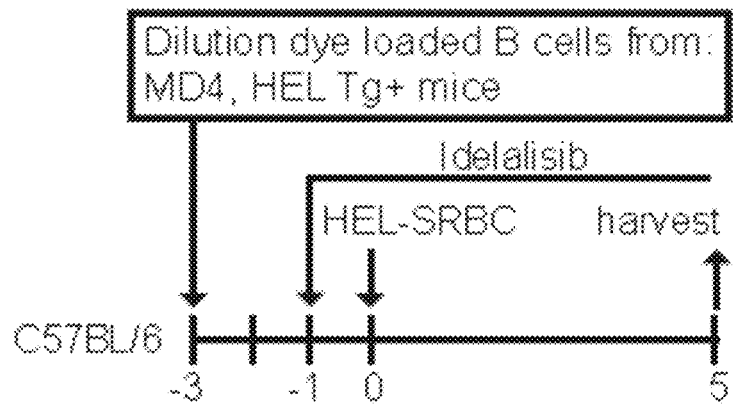
FIGS. 5A-5G show dose-dependent idelalisib inhibition of antibody responses.
Figure 5G:
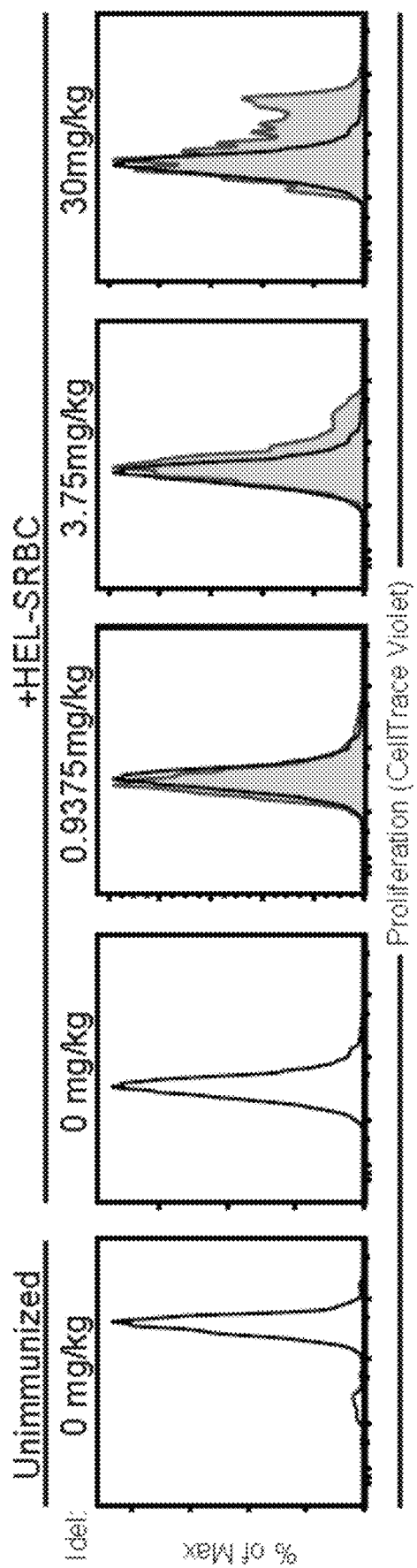
Figure 5B:
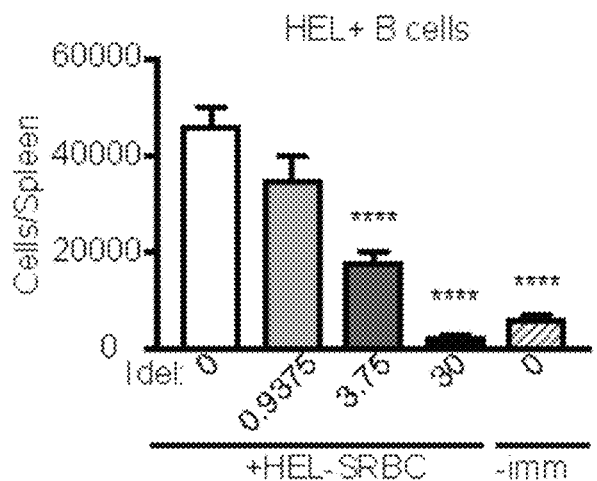
Figure 5C:
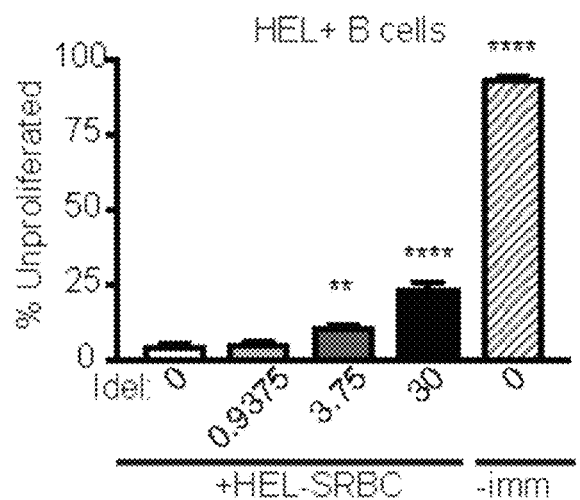
Figure 5D:
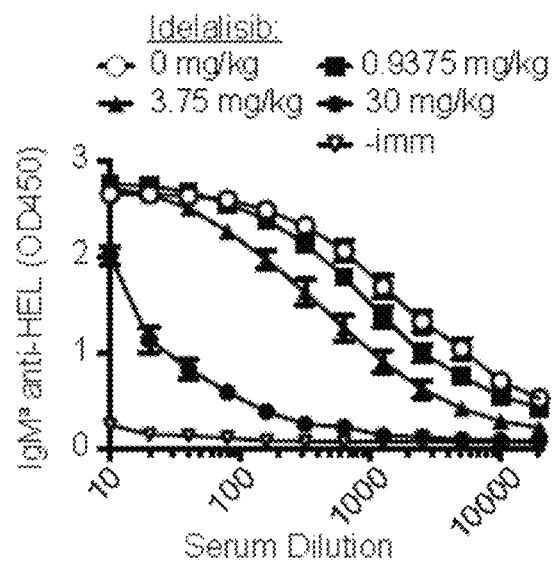
Figure 5E:
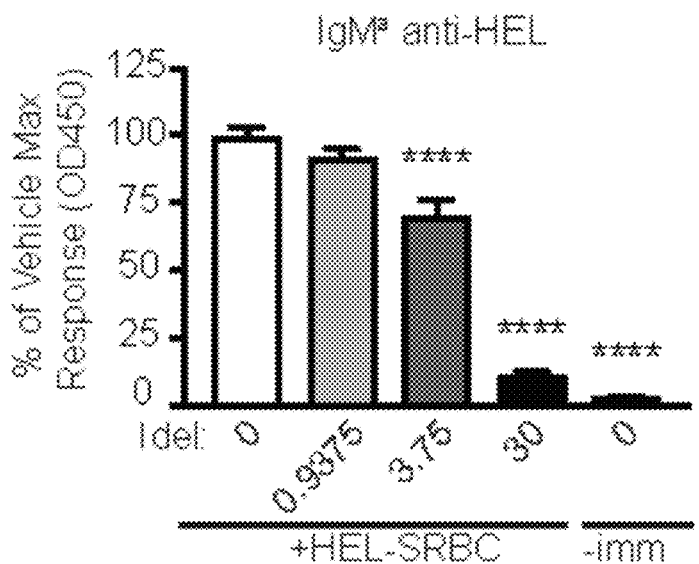
Figure 5F:
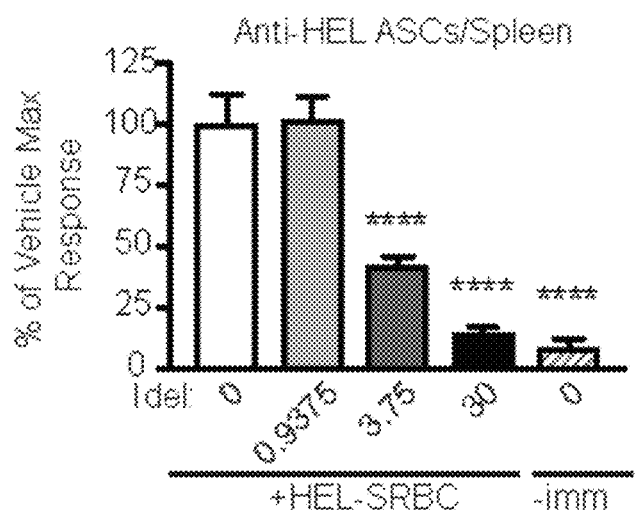

As shown in FIG. 1, low dose idelalisib does not inhibit antibody responses in NOD mice. To investigate this further the effect of a range of idelalisib doses on in vivo B cell responses to immunization was investigated. MD4 B cells loaded with dilution dye were adoptively transferred into C57BL/6 recipients, and, after allowing the cells to rest for 48 hours, recipient mice were placed on various doses of idelalisib-containing chow. Twenty-four hours later, the inventors immunized with HEL conjugated to SRBC, and analyzed the B cell response 5 days later (FIG. 5A). MD4 B cells from mice receiving vehicle control chow and 0.9375 mg/kg idelalisib-containing chow mounted equivalent IgM anti-HEL antibody responses and generated equivalent HEL-specific ASCs/spleen (FIGS. 5D, 5E, and 5F). MD4 B cells in mice receiving 3.75 mg/kg and 30 mg/kg idelalisib-containing chow prior to immunization mounted significantly reduced IgM anti-HEL antibody responses and generated a reduced number of ASCs/spleen in comparison to MD4 B cells from vehicle control cohorts (FIGS. 5D, 5E, and 5F). This dose-dependent reduction in HEL-specific antibody is further reflected in the recovery of MD4 B cells in the spleens of mice from the various cohorts. Mice receiving 3.75 mg/kg and 30 mg/kg idelalisib containing chow had significant decreases in recoverable transferred cells, while recovered cells proliferated less than in controls (FIGS. 5B, 5G, quantified FIG. 5C). These data clearly define doses that enforce anergy of autoreactive B cells while sparing B cell responses to exogenous antigen.

Example 7

Low Dose p110δ Inhibition does not Inhibit T Cell Responses In Vitro or In Vivo

T cells are essential components of antibody responses to most proteinaceous antigens, including autoantigens. T cells utilize the p110δ isoform, but the role of low dose inhibition of this isoform on T cell function has not been studied. Studies of p110δ knockout mice or functionally inactive p110δ mice have yielded conflicting results with respect to the requirement of this isoform for T cell responses. Autoantibody responses caused here by compromise of Ars/A1 anti-chromatin B cells is T cell dependent. Upon transfer into TCRα$^{-/-}$ recipients these B cells fail to proliferate, differentiate and secrete autoantibody. This raises the possibility that idelalisib is mediating its effect by inhibiting T cell function. It is noteworthy, however, that if this were the case, the inhibitor should have been equally effective in inhibiting autoimmunity caused by B cell targeted PTEN$^{-/+}$×SHIP-1$^{-/+}$ and SHP-1$^{-/-}$ conditions. Nonetheless, the inventors set out to determine the consequence of low dose p110δ inhibition on T cell responses in vitro and in vivo.

Figure 6A:
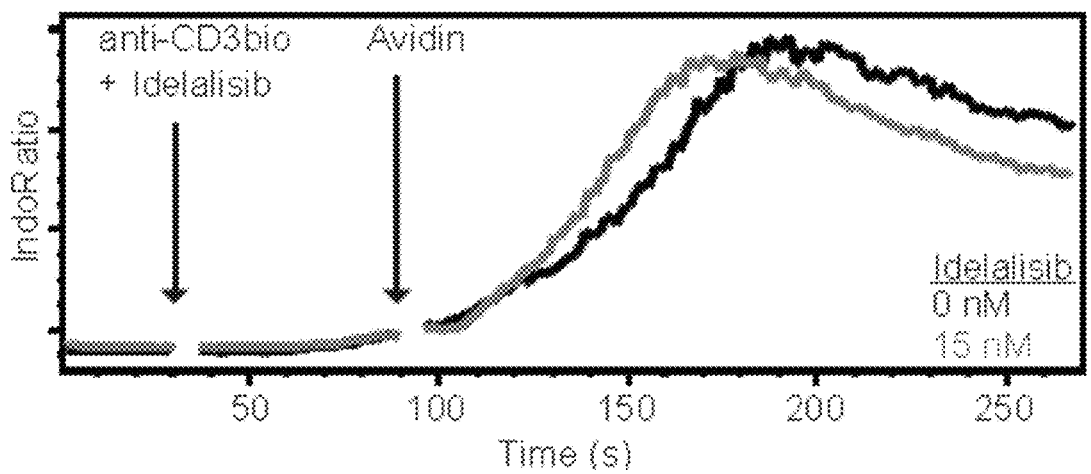
FIGS. 6A-6F show low dose p110δ inhibition does not inhibit CD4+ T cell responses in vitro or in vivo.
Figure 6B:
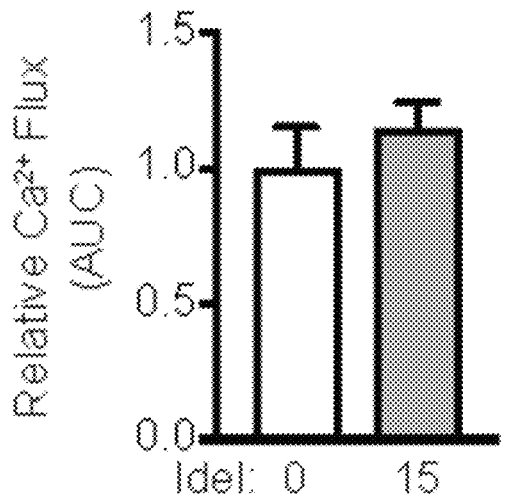
Figure 6C:
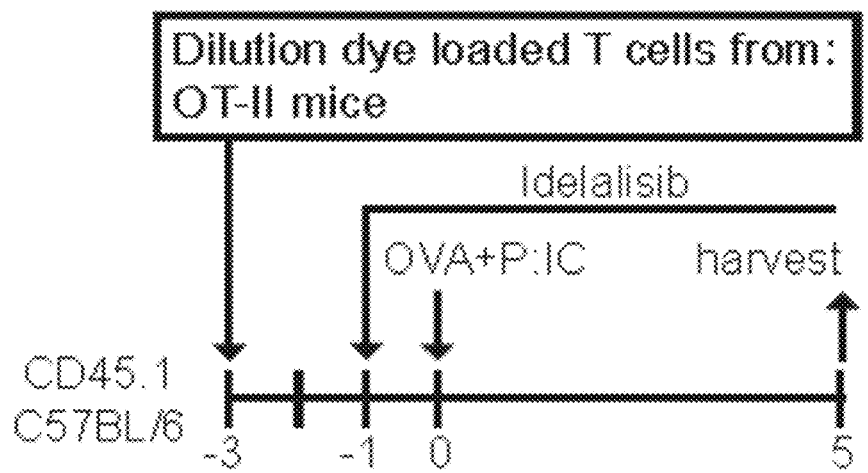
Figure 6D:
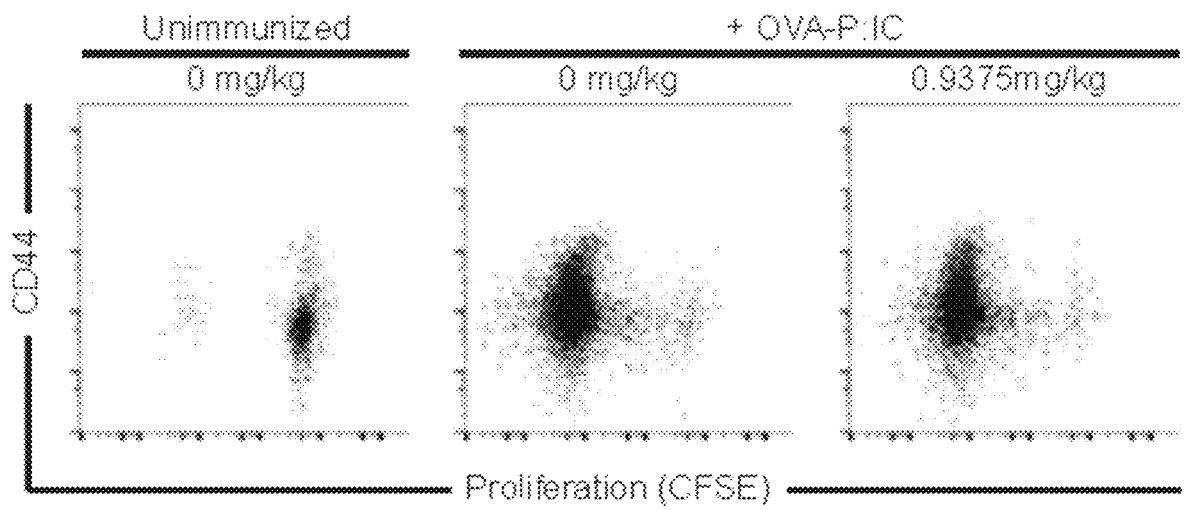
Figure 6E:
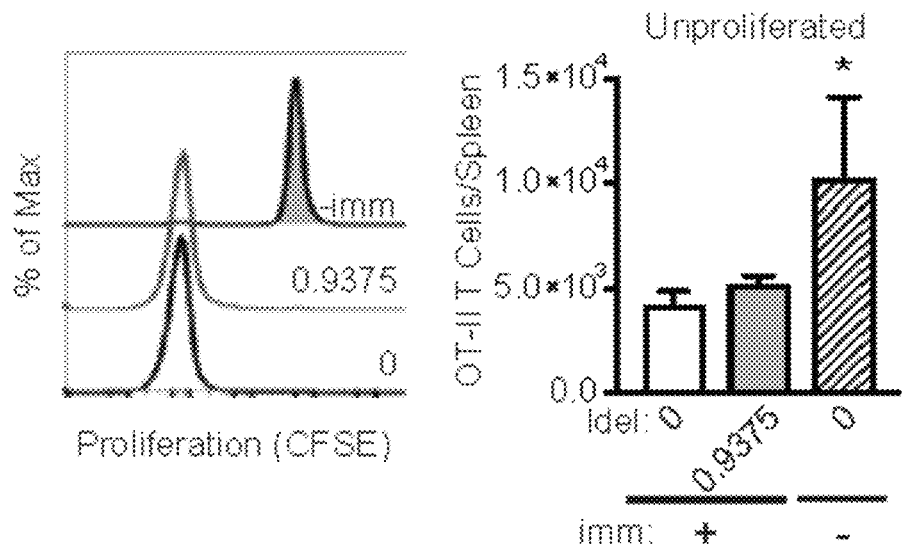
Figure 6F:
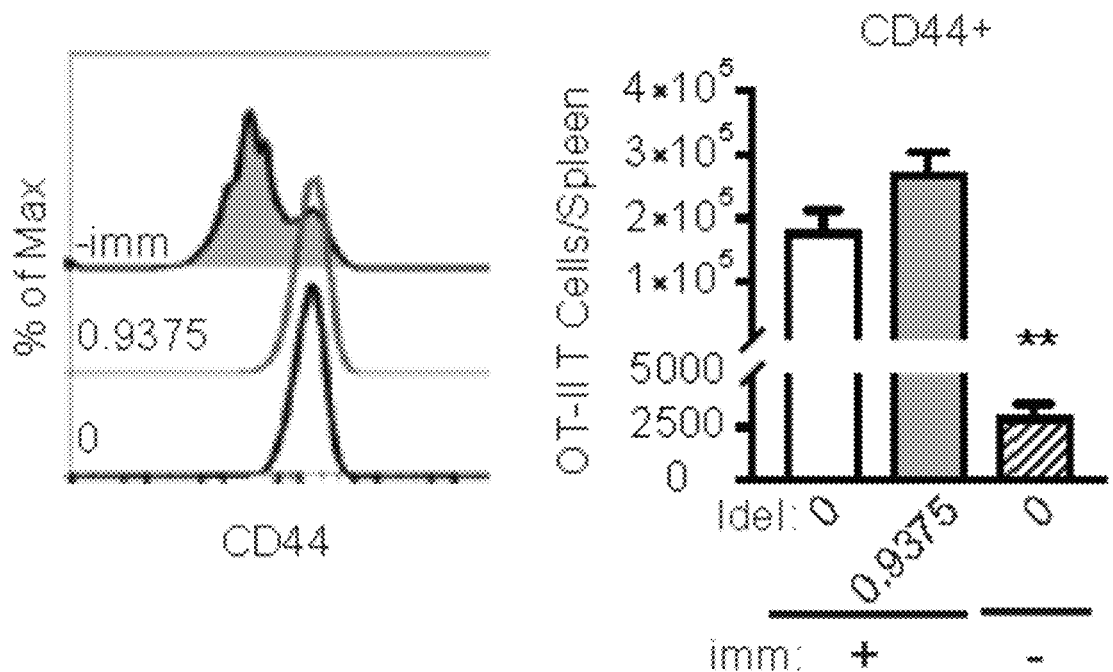

Because a therapeutic effect of the inhibitor on VH125.NOD disease progression and survival was observed, reduction in autoantibody responses in PTEN$^{-/+}$× SHIP-1$^{-/+}$ cells, yet equivalent autoantibody responses by SHP-1$^{-/-}$ and MD4 B cells in mice receiving 0.9375 mg/kg idelalisib-containing chow, we chose to focus our analysis on effects of this dose on T cell function. 15 nM idelalisib (the in vitro equivalent to 0.9375 mg/kg), failed to inhibit calcium mobilization of CD4 T cells stimulated by TCR aggregation with biotin-anti-CD3 and avidin (FIG. 6A, quantified in FIG. 6B). To analyze in vivo CD4 T cell responses, OT-II CD4 T cells were adoptively transferred into congenically mismatched recipients and immunized with OVA+P:IC as represented diagrammatically in FIG. 6C. Five days post-immunization with OVA+P:IC, mice that received vehicle control chow and mice that received 0.9375 mg/kg idelalisib containing chow proliferated (FIG. 6E left panel, quantified right panel), and upregulated the activation marker CD44 to equivalent levels (FIG. 6F left panel, quantified right panel). The transferred OT-II cells that proliferated most underwent the greatest upregulation of CD44 (FIG. 6D). Doses of idelalisib that enforce anergy of autoreactive B cells, delay disease progression and prolong survival in VH125.NOD mice do not affect CD4 T cell responses in vitro or in vivo.

The various features and processes described above may be used independently of one another or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method of treating or delaying the onset or slowing the progression of an autoimmune disease or disorder in a subject comprising administering a therapeutically effective amount of a phosphoinositide 3-kinase p110-delta (PI3K-p110δ) inhibitor to the subject at a dosage that does not reduce immune response to exogenous immunogens in the subject.

2. The method of claim 1, wherein the PI3K-p110δ inhibitor is idelalisib.

3. The method of claim 2, wherein the idelalisib is administered at a dosage of between about 0.23 mg/kg/day and about 3.6 mg/kg/day.

4. The method of claim 2, wherein the idelalisib is administered at a dosage of between about 0.45 mg/kg/day and about 1.8 mg/kg/day.

5. The method of claim 2, wherein the idelalisib is administered at a dosage of between about 0.9 mg/kg/day and about 1.8 mg/kg/day.

6. The method of claim 2, wherein the idelalisib is administered at a dosage of between about 1.8 mg/kg/day and about 3.6 mg/kg/day.

7. The method of claim 2, wherein the idelalisib is administered at a dosage of about 0.9 mg/kg/day.

8. The method of claim 2, wherein the idelalisib is administered at a dosage of about 1.8 mg/kg/day.

9. The method of claim 1, wherein the autoimmune disease or disorder is selected from autoimmune diabetes mellitus (type 1 diabetes mellitus; TID), systemic lupus erythematosus, autoimmune thyroiditis, rheumatoid arthritis, psoriasis, and multiple sclerosis.

10. The method of claim 1, wherein the autoimmune disease is type 1 diabetes mellitus (TID).

* * * * *